United States Patent
Fu

(10) Patent No.: US 10,398,905 B2
(45) Date of Patent: Sep. 3, 2019

(54) USES OF POROUS NANOSTRUCTURE IN DELIVERY

(71) Applicant: NVIGEN, INC., Sunnyvale, CA (US)

(72) Inventor: Aihua Fu, Sunnyvale, CA (US)

(73) Assignee: NVIGEN, INC., Sunnyvale, CA (US)

( * ) Notice: Subject to any disclaimer, the term of this patent is extended or adjusted under 35 U.S.C. 154(b) by 0 days.

(21) Appl. No.: 14/379,495

(22) PCT Filed: Feb. 19, 2013

(86) PCT No.: PCT/US2013/026756
§ 371 (c)(1),
(2) Date: Aug. 19, 2014

(87) PCT Pub. No.: WO2013/123523
PCT Pub. Date: Aug. 22, 2013

(65) Prior Publication Data
US 2015/0037249 A1    Feb. 5, 2015

Related U.S. Application Data

(60) Provisional application No. 61/600,696, filed on Feb. 19, 2012.

(51) Int. Cl.
| | |
|---|---|
| *A61K 9/51* | (2006.01) |
| *A61N 2/00* | (2006.01) |
| *A61K 9/00* | (2006.01) |
| *A61K 47/02* | (2006.01) |
| *A61K 31/7088* | (2006.01) |
| *A61K 38/12* | (2006.01) |
| *A61M 31/00* | (2006.01) |
| *A61K 47/69* | (2017.01) |

(52) U.S. Cl.
CPC ............ *A61N 2/002* (2013.01); *A61K 9/0009* (2013.01); *A61K 9/0019* (2013.01); *A61K 9/5115* (2013.01); *A61K 31/7088* (2013.01); *A61K 38/12* (2013.01); *A61K 47/02* (2013.01); *A61K 47/6923* (2017.08); *A61M 31/00* (2013.01)

(58) Field of Classification Search
CPC ........ A61K 9/51; A61K 9/5107; A61K 9/141; A61K 51/00; A61K 51/02; A61K 51/04; A61K 51/08; A61K 51/10
See application file for complete search history.

(56) References Cited

U.S. PATENT DOCUMENTS

| | | | |
|---|---|---|---|
| 7,329,638 B2 * | 2/2008 | Yang | A61K 47/4823 424/185.1 |
| 2003/0129130 A1 * | 7/2003 | Guire | A61K 9/2081 424/1.11 |
| 2004/0076681 A1 | 4/2004 | Dennis et al. | |
| 2004/0213986 A1 * | 10/2004 | Kim | B82Y 5/00 428/315.7 |
| 2005/0042753 A1 | 2/2005 | Yang et al. | |
| 2006/0127480 A1 * | 6/2006 | Tobyn | A61K 9/143 424/484 |
| 2010/0061937 A1 | 3/2010 | Magnani et al. | |
| 2012/0021036 A1 | 1/2012 | Majeti et al. | |
| 2012/0128958 A1 * | 5/2012 | Zeng | C01B 33/1585 428/219 |

FOREIGN PATENT DOCUMENTS

| | | |
|---|---|---|
| WO | 2009/021286 A1 | 2/2009 |
| WO | 2011/130716 A2 | 10/2011 |

OTHER PUBLICATIONS

K.C. Souza et al. "Study of mesoporous silica/magnetite systems in drug controlled release" J Mater Sci: Mater Med (2009) 20: 507-512.
Wufeng Chen et al. "Self-Assembly and Embedding of Nanoparticles by In Situ Reduced Graphene for Preparation of a 3D Graphene/Nanoparticle Aerogel" Adv. Mater. 2011, 23, 5679-5683.

* cited by examiner

*Primary Examiner* — Micah Paul Young
(74) *Attorney, Agent, or Firm* — Jun He Law Offices P.C.; James J. Zhu

(57) ABSTRACT

The present invention relates to methods for delivering at least one agent unto or into a biological sample or a biological subject. The methods comprise a step of contacting the biological sample or subject with a payload-carrying nanostructure. The nanostructure can be a porous low density nanostructure.

20 Claims, 5 Drawing Sheets

| (a) 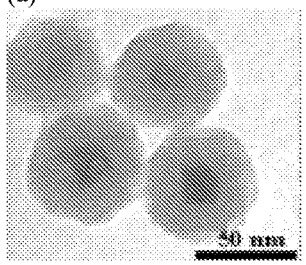 From Viswagen (www.viswagenbiotech.com) product description: TEM of nanoparticles containing magnetic core and silica shell component. This is for their products of magnetic and fluorescent nanoparticles. The silica structure is clearly observable under TEM. | (d) 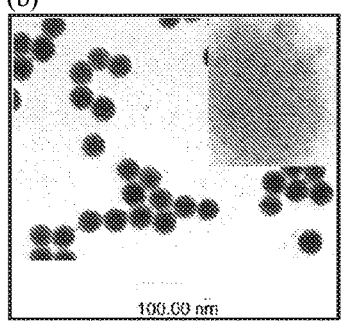 TEM micrograph of mesoporous silica nanoparticles synthesized from prof. Christy L. Hayne's group. The siliceous structure is clearly observable under TEM. (J. Am. Chem. Soc., 2011, 133, 20444-20457.) |
|---|---|
| (b) 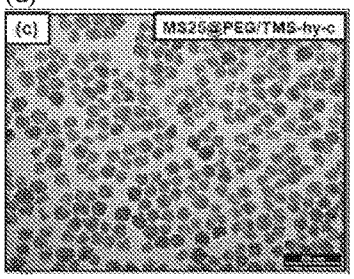 TEM micrograph of luminophore doped silica nanoparticles prepared by Prof. Weihong Tan's group. These silica nanoparticles could be clearly observed under TEM. (Anal. Chem. 2001, 73, 4988-4993.) | (e) 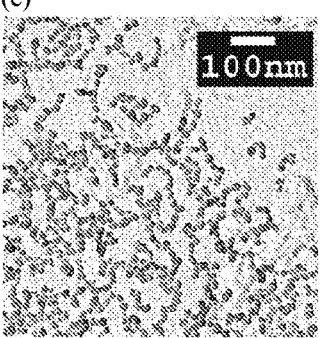 TEM micrograph of fluorescent silica nanoparticles by incorporating organic fluorophores within a siliceous structure from Prof. Ulrich Wiesner's group. the siliceous structure is clearly observable under TEM. (Nano letters, 2005, 5, 113.) |

USES OF POROUS NANOSTRUCTURE IN DELIVERY

CROSS-REFERENCE TO RELATED APPLICATIONS

The present application claims the benefit of U.S. Provisional Patent Application No. 61/600,696 filed on Feb. 19, 2012, which is incorporated herein by reference in its entirety.

BACKGROUND

Nanoparticles provide a wide range of applications in fields such as molecular imaging, early stage diagnosis and targeted therapy. It is challenging but desirable to design and prepare nanoparticles that are capable of incorporating or carrying a large amount of payloads and being delivered into a biological sample. Therefore, there are needs to continue to develop such nanoparticles.

SUMMARY OF THE INVENTION

One aspect of the present disclosure relates to compositions comprising a payload-carrying nanostructure and a biological sample. In certain embodiments, the nanostructure comprises at least one core nanoparticle embedded in or coated with a low density porous 3-D structure or coating, which is capable of carrying or associating with at least one payload within or on the surface of the nanostructure.

In certain embodiments, the core nanoparticle comprises a nanoparticle or a cluster of nanoparticles. A single core nanoparticle may comprise a plurality or a cluster of mini-nanoparticles. The nanoparticles in the cluster may be made by the same composition, or different compositions.

In certain embodiments, the core nanoparticle includes, for example, a superparamagnetic iron oxide (SPIO) nanoparticle, or a non-SPIO nanoparticle. The non-SPIO nanparticles include, for example, metallic nanoparticles (e.g., gold or silver nanoparticles), a metal oxide nanoparticle, semiconductor nanoparticle (e.g., quantum dots with individual or multiple components such as CdSe/ZnS, doped heavy metal free quantum dots or other semiconductor quantum dots); polymeric nanoparticles (e.g., particles made of one or a combination of PLGA (poly(lactic-co-glycolic acid), PCL (polycaprolactone), PEG (poly ethylene glycol) or other polymers); siliceous nanoparticles; and non-SPIO magnetic nanoparticles (e.g., MnFe2O4, SAF, and other types of magnetic nanoparticles). The core nanoparticle has a diameter ranging from about 1 nm to about 900 nm (preferable 1-50 nm, 2-40 nm, 5-20 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm in size).

In certain embodiments, the core nanoparticle has a shape of sphere, rod, tetrapod, pyramidal, multi-armed, nanotube, nanowire, nanofiber, or nanoplate.

In certain embodiments, the low density, porous 3-D structure refers to a structure with density at least 10s times (e.g. 10s times, 20s times, 30s times, 50s times, 70s times, 100s times, 1000s times, 10,000 times) lower than existing mesoporous materials (e.g. mesoporous materials having a pore size ranging from 2 nm to 50 nm). In certain embodiments, the low density, porous 3-D structure has a density of <1.0 g/cc (e.g. from 0.01 mg/cc to 1000 mg/cc). In certain embodiments, the density is determined using dry mass of the 3-D structure divided by the total volume of such 3-D structure in an aqueous solution.

In certain embodiments, the low density, porous 3-D structure is highly porous. Such low density structure further refers to a structure having at least 40% to at least 99.9% (preferably 50% to 99.9%) of empty space or porosity in the structure. In certain embodiments, at least 80% of the pores having size of 1 nm to 500 nm in pore radius.

In certain embodiments, the low density, porous 3-D structure is a structure that can not be obviously observed or substantially invisible under transmission electron microscope, for example, even when the feature size of the low density structure is in the 10s or 100s nanometer range.

In certain embodiments, the low density, porous 3-D structure is made of silicon-containing molecules (e.g., silanes, organosilanes, alkoxysilanes, silicates and derivatives thereof). For example, the silicon-containing molecules can be amino-propyl-trimethoxysilane, mercapto-propyl-trimethoxysilane, carboxyl-propyl-trimethoxysilane, amino-propyl-triethoxysilane, mercapto-propyl-triethoxysilane, carboxyl-propyl-triethoxysilane, Bis-[3-(triethoxysilyl) propyl]-tetrasulfide, Bis[3-(triethoxysilyl) propyl]-disulfide, aminopropyltriethoxysilane, N-2-(aminoethyl)-3-amino propyltrimethoxysilane, Vinyltrimethoxysilane, Vinyl-tris(2-methoxyethoxy) silane, 3-methacryloxypropyl-trimethoxy silane, 2-(3,4-epoxycyclohexy)-ethyl trimethoxysilane, 3-glycidoxy-propyltriethoxysilane, 3-isocyanatopropyltriethoxysilane, 3-cyanatopropyltriethoxysilane, and sodium silicates.

In certain embodiments, the low density, porous 3-D structure is associated with the core nanoparticle via intra-molecular interaction (e.g. covalent bonds, metallic bonds, and/or ionic bonding) or inter-molecular interaction (e.g. hydrogen bond, and/or non covalent bonds).

In certain embodiments, the low density, porous 3-D structure is a stable crosslinked coating with thickness ranging from 1 nm to 1000 nm (e.g. from 1 nm to 500 nm). In certain embodiments, the thickness of the low density, porous 3-D structure is controllable, so is the number of payloads that could be carried. As a result, the nanostructures when systematically applied as injectable agents into the blood stream of a living subjects can accumulate at a disease region, such as a tumor or inflammation site. In certain embodiments, the nanostructure is capable of carrying or being associated with one or more payloads. In certain embodiments, the payloads to be carried or associated with the nanostructure include, but are not limited to, a detectable agent (e.g. a fluorescent molecule, a chemo-luminescent molecule, a bio-luminescent molecule, a radioisotope, a MRI contrast agent, a CT contrast agent, an enzyme-substrate label, and/or a coloring agent), a targeting moiety (e.g. an antibody, an antigen, a ligand, an aptamer, a peptide, a nucleic acid, a polynucleotide, a polysaccharide, sugar, fatty acid, steroids, pyrimidines, and/or a hapten), a binding partner (e.g. antigen, antibody, receptor, ligand, DNA, RNA, peptide, aptamer, biotin, avidin, streptavidin, lectin, carbohydrate, Protein A, antibody Fc, desthiobiotin, and/or iminobiotin), a biological active agent (e.g. therapeutic agents, proteins, antibodies, peptides, nucleic acids, enzymes, thermal-responsive molecules, optical-responsive molecules, electronic-responsive molecules, magnetic-responsive molecules, pH-responsive molecules, enzymatic responsive molecules and/or chemical compounds), a drug, a therapeutic agent, a radiological agent, a chemological agent, a small molecule drug, a biological drug (e.g., peptides, proteins, antibodies, antigens, nucleic acids, aptamers and the like) and combinations thereof, which can be used to image, detect, study, monitor, evaluate, screen a disease, condition, and/or related biological event. In certain embodiments, the nanostructure comprises a first payload and a second payload.

Another aspect of the present disclosure relates to methods of delivering at least one agent unto or into a biological sample comprising a step of contacting a biological sample with the payload-carrying nanostructure provided herein.

In certain embodiments, the nanostructure has magnetic property so as to enhance the delivery using magnetic interaction.

In certain embodiments, the payload-carrying nanostructure comprises a first payload. In certain embodiments, the payload-carrying nanostructure further comprises a second payload. In certain embodiments, the first payload and the second payload are randomly or orientedly distributed in the nanostructure.

In certain embodiments, the surface of the nanostructure is modulated with molecular entities that facilitate the delivery function, wherein as the entities improve specific targeting functions, reduce non-specific association, or adjust the density of payloads on surface.

In certain embodiments, the size of the nanostructure is tailored from 1 nm to 1000 nm to optimize its delivery function. In certain embodiments, the charge of the nanostructure is tuned to optimize its delivery function.

In certain embodiments, the nanostructure is biocompatible and can be formed by a physiologically acceptable component material. The nanostructure may be biodegradable.

In certain embodiments, the payload is released into the biological sample via electrostatic principals, biological or enzymatic interactions, or through photo, pH, thermal, or electronic sensitive bonds.

Another aspect of the present disclosure relates to methods of delivering at least one agent onto or cross a biological barrier comprising a step of contacting a biological barrier with a payload-carrying nanostructure.

Another aspect of the present disclosure relates to compositions comprising a payload-carrying nanostructure having a payload and a biological sample.

DESCRIPTION OF THE DRAWINGS

FIG. 6(a) shows the bright field image showing the cell, FIG. 6(b) shows the fluorescent image showing DNA inside cells.

FIG. 7(a) shows the image of the cells incubated with no magnet, and there are not much nanoparticles inside cells. FIG. 7(b) shows the image of the cells incubated with a magnet, and accordingly, much more nanoparticles were observed inside the cells for magnetically improved nanoparticle delivery. FIG. 7(c) shows the quantity of the cells and the quantity of the nanoparticles delivered into the cells, in the presence or absence of a magnet. "Total cell" means the number of total cells counted, "Total NP" means the total number of nanostructures counted, and "Average" means the average number of nanostructures per cell.

DETAILED DESCRIPTION OF THE INVENTION

Figure 1:
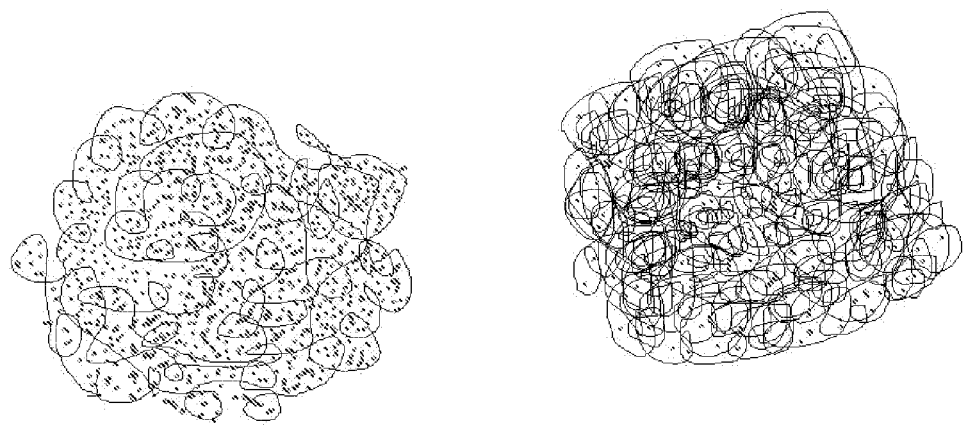
FIG. 1. A schematic comparison of low density nanostructure (LDNS) incorporating a plurality of payloads (dots) with dense nanostructures (black network, right).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, solid state chemistry, inorganic chemistry, organic chemistry, physical chemistry, analytical chemistry, materials chemistry, biochemistry, biology, molecular biology, recombinant DNA techniques, pharmacology, imaging, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

The following embodiments are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

One aspect of the present disclosure relates to porous nanostructures as disclosed in U.S. Prov. Appl. 61/589,777, which is incorporate herein, and the uses thereof in delivering payloads onto or into biological samples.

Porous Nanostructures

In certain embodiments, the porous nanostructure comprises at least one core nanoparticle embedded in or coated with a low density, porous 3-D structure.

The core nanoparticle used herein includes, but not limited to, a superparamagnetic iron oxide (SPIO) nanoparticle, and a non-SPIO nanoparticle.

The SPIO nanoparticle is an iron oxide nanoparticle, either maghemite ($\gamma$-$Fe_2O_3$) or magnetite ($Fe_3O_4$), or nanoparticles composed of both phases. The SPIO can be synthesized with a suitable method and dispersed as a colloidal solution in organic solvents or water. Methods to synthesize the SPIO nanoparticles are known in the art (see, for example, Morteza Mahmoudi et al, Superparamagnetic Iron Oxide Nanoparticles: Synthesis, Surface Engineering, Cytotoxicity and Biomedical Applications, published by Nova Science Pub Inc, 2011). In one embodiment, the SPIO nanoparticles can be made through wet chemical synthesis methods which involve co-precipitation of $Fe^{2+}$ and $Fe^{3+}$ salts in the presence of an alkaline medium. During the synthesis, nitrogen may be introduced to control oxidation, surfactants and suitable polymers may be added to inhibit agglomeration or control particle size, and/or emulsions (such as water-in-oil microemulsions) may be used to modulate the physical properties of the SPIO nanoparticle (see, for example, Jonathan W. Gunn, The preparation and characterization of superparamagnetic nanoparticles for biomedical imaging and therapeutic application, published by ProQuest, 2008). In another embodiment, the SPIO nanoparticles can be generated by thermal decomposition of iron pentacarbonyl, alone or in combination with transition metal carbonyls, optionally in the presence of one or more surfactants (e.g. lauric acid and oleic acid) and/or oxidatants (e.g. trimethylamine-N-oxide), and in a suitable solvent (e.g. dioctyl ether or hexadecane) (see, for example, US patent application 20060093555). In another embodiment, the SPIO nanoparticles can also be made through gas deposition methods, which involves laser vaporization of iron in a helium atmosphere containing different concentrations of oxygen (see, Miller J. S. et al., Magnetism: Nanosized magnetic materials, published by Wiley-VCH, 2002).

In certain embodiments, the SPIO nanoparticles are those disclosed in US patent application US20100008862.

The non-SPIO nanoparticles include, for example, metallic nanoparticles (e.g., gold or silver nanoparticles (see, e.g., Hiroki Hiramatsu, F.E.O., *Chemistry of Materials* 16, 2509-2511 (2004)), semiconductor nanoparticles (e.g., quantum dots with individual or multiple components such as CdSe/ZnS (see, e.g., M. Bruchez, et al., *science* 281, 2013-2016 (1998))), doped heavy metal free quantum dots (see, e.g., Narayan Pradhan et al, *J. Am. chem. Soc.* 129, 3339-3347 (2007)) or other semiconductor quantum dots); polymeric nanoparticles (e.g., particles made of one or a combination of PLGA (poly(lactic-co-glycolic acid) (see, e.g., Minsoung Rhee et al., *Adv. Mater.* 23, H79-H83 (2011)), PCL (polycaprolactone) (see, e.g., Marianne Labet et al., *Chem. Soc. Rev.* 38, 3484-3504 (2009)), PEG (poly ethylene glycol) or other polymers); siliceous nanoparticles; and non-SPIO magnetic nanoparticles (e.g., $MnFe_2O_4$ (see, e.g., Jae-Hyun Lee et al., *Nature Medicine* 13, 95-99 (2006)), synthetic antiferromagnetic nanoparticles (SAF) (see, e.g., A. Fu et al., *Angew. Chem. Int. Ed.* 48, 1620-1624 (2009)), and other types of magnetic nanoparticles).

The non-SPIO nanoparticles can be prepared or synthesized using suitable methods known in the art, such as for example, sol-gel synthesis method, water-in-oil micro-emulsion method, gas deposition method and so on. For example, gold nanoparticles can be made by reduction of chloroaurate solutions (e.g. $HAuCl_4$) by a reducing agent such as citrate, or acetone dicarboxylate. For another example, CdS semiconductor nanoparticle can be prepared from $Cd(ClO_4)_2$ and $Na_2S$ on the surface of silica particles. For another example, II-VI semiconductor nanoparticles can be synthesized based on pyrolysis of organometallic reagents such as dimethyl cadmium and trioctylphosphine selenide, after injection into a hot coordinating solvent (see, e.g. Günter Schmid, Nanoparticles: From Theory to Application, published by John Wiley & Sons, 2011). Doped heavy metal free quantum dots, for example Mn-doped ZnSe quantum dots can be prepared using nucleation-doping strategy, in which small-sized MnSe nanoclusters are formed as the core and ZnSe layers are overcoated on the core under high temperatures. For another example, polymeric nanoparticles can be prepared by emulsifying a polymer in a two-phase solvent system, inducing nanosized polymer droplets by sonication or homogenization, and evaporating the organic solvent to obtain the nanoparticles. For another example, siliceous nanoparticles can be prepared by sol-gel synthesis, in which silicon alkoxide precursors (e.g. TMOS or TEOS) are hydrolyzed in a mixture of water and ethanol in the presence of an acid or a base catalyst, the hydrolyzed monomers are condensed with vigorous stirring and the resulting silica nanoparticles can be collected. For another example, SAFs, a non-SPIO magnetic nanoparticle, can be prepared by depositing a ferromagenetic layer on each of the two sides of a nonmagnetic space layer (e.g. ruthenium metal), along with a chemical etchable copper release layer and protective tantalum surface layers, using ion-bean deposition in a high vacuum, and the SAF nanoparticle can be released after removing the protective layer and selective etching of copper.

The size of the core nanoparticles ranges from 1 nm to 100 nm in size (preferable 1-50 nm, 2-40 nm, 5-20 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm in size). The size of nanoparticles can be controlled by selecting appropriate synthesis methods and/or systems. For example, to control the size of nanoparticles, synthesis of nanoparticles can be carried out in a polar solvent which provides ionic species that can adsorb on the surface of the nanoparticles, thereby providing electrostatic effect and particle-particle repulsive force to help stabilize the nanoparticles and inhibit the growth of the nanoparticles. For another example, nanoparticles can be synthesized in a micro-heterogeneous system that allows compartmentalization of nanoparticles in constrained cavities or domains. Such a micro-heterogeneous system may include, liquid crystals, mono and multilayers, direct micelles, reversed micelles, microemulsions and vesicles. To obtain nanoparticles within a desired size range, the synthesis conditions may be properly controlled or varied to provide for, e.g., a desired solution concentration or a desired cavity range (a detailed review can be found at, e.g. Vincenzo Liveri, Controlled synthesis of nanoparticles in microheterogeneous systems, Published by Springer, 2006).

The shape of the core nanoparticles can be spherical, cubic, rod shaped (see, e.g., A. Fu et al., *Nano Letters*, 7, 179-182 (2007)), tetrapo-shaped (see, e.g., L. Manna et al., *Nature Materials*, 2, 382-385 (2003)), pyramidal, multi-armed, nanotube, nanowire, nanofiber, nanoplate, or any other suitable shapes. Methods are known in the art to control the shape of the nanoparticles during the preparation (see, e.g. Waseda Y. et al., Morphology control of materials and nanoparticles: advanced materials processing and characterization, published by Springer, 2004). For example, when the nanoparticles are prepared by the bottom-up process (i.e. from molecule to nanoparticle), a shape controller which adsorbs strongly to a specific crystal plane may be added to control the growth rate of the particle.

A single core nanoparticle may comprise a single nanoparticle or a plurality or a cluster of mini-nanoparticles (A. Fu et al., *J. Am. chem. Soc.* 126, 10832-10833 (2004), J. Ge et al., *Angew. Chem. Int. Ed.* 46, 4342-4345 (2007), Zhenda Lu et al., *Nano Letters* 11, 3404-3412 (2011).). The mini-nanoparticles can be homogeneous (e.g., made of the same composition/materials or having same size) or heterogeneous (e.g., made of different compositions/materials or having different sizes). A cluster of homogeneous mini-nanoparticles refers to a pool of particles having substantially the same features or characteristics or consisting of substantially the same materials. A cluster of heterogeneous mini-nanoparticles refers to a pool of particles having different features or characteristics or consisting of substantially different materials. For example, a heterogeneous mini-nanoparticle may comprise a quantum dot in the center and a discrete number of gold (Au) nanocrystals attached to the quantum dot. Different nanoparticles in a heterogeneous nanoparticle pool do not need to associate with each other at first, but rather, they could be individually and separately associated with the low density porous structure.

In certain embodiments, a nanostructure disclosed comprising a plurality of core nanoparticles embedded in or coated with a low density, porous 3-D structure. For example, the nanostructure contains 2, 3, 4, 5, 6, 7, 8, 9, 10, 11, 12, 13, 14, 15, 16, 17, 18, 19, 20, 25, 30, 35, 40, 50, 60, 70, 80, 90, 100, 100s or 1000s core nanoparticles.

In certain embodiments, the low density, porous 3-D structure refers to a structure with density much lower (e.g. 10s times, 20s times, 30s times, 50s times, 70s times, 100s times) than existing mesoporous nanoparticles (e.g. mesoporous nanoparticles having a pore size ranging from 2 nm to 50 nm). (A. Vincent, et. al., J. Phys. Chem. C, 2007, 111, 8291-8298. J. E. Lee, et. al., J. Am. Chem. Soc., 2010, 132, 552-557. Y.-S. Lin, et. al., J. Am. Chem. Soc., 2011, 133, 20444-20457. Z. Lu, Angew. Chem. Int. Ed., 2010, 49, 1862-1866.)

In certain embodiments, the low density, porous 3-D structure refers to a structure having a density of <1.0 g/cc (e.g., <100 mg/cc, <10 mg/cc, <5 mg/cc, <1 mg/cc, <0.5 mg/cc, <0.4 mg/cc, <0.3 mg/cc, <0.2 mg/cc, or <0.1 mg/cc) (for example, from 0.01 mg/cc to 10 mg/cc, from 0.01 mg/cc to 8 mg/cc, from 0.01 mg/cc to 5 mg/cc, from 0.01 mg/cc to 3 mg/cc, from 0.01 mg/cc to 1 mg/cc, from 0.01 mg/cc to 1 mg/cc, from 0.01 mg/cc to 0.8 mg/cc, from 0.01 mg/cc to 0.5 mg/cc, from 0.01 mg/cc to 0.3 mg/cc, from 0.01 mg/cc to 1000 mg/cc, from 0.01 mg/cc to 915 mg/cc, from 0.01 mg/cc to 900 mg/cc, from 0.01 mg/cc to 800 mg/cc, from 0.01 mg/cc to 700 mg/cc, from 0.01 mg/cc to 600 mg/cc, from 0.01 mg/cc to 500 mg/cc, from 0.1 mg/cc to 800 mg/cc, from 0.1 mg/cc to 700 mg/cc, from 0.1 mg/cc to 1000 mg/cc, from 1 mg/cc to 1000 mg/cc, from 5 mg/cc to 1000 mg/cc, from 10 mg/cc to 1000 mg/cc, from 20 mg/cc to 1000 mg/cc, from 30 mg/cc to 1000 mg/cc, from 30 mg/cc to 1000 mg/cc, from 30 mg/cc to 900 mg/cc, from 30 mg/cc to 800 mg/cc, or from 30 mg/cc to 700 mg/cc).

The density of 3-D structure can be determined using various methods known in the art (see, e.g., Lowell, S. et al., Characterization of porous solids and powders: surface area, pore size and density, published by Springer, 2004). Exemplary methods include, Brunauer Emmett Teller (BET) method and helium pycnometry (see, e.g., Varadan V. K. et al., Nanoscience and Nanotechnology in Engineering, published by World Scientific, 2010). Briefly, in BET method, dry powders of the testing 3-D structure is placed in a testing chamber to which helium and nitrogen gas are fed, and the change in temperature is recorded and the results are analyzed and extrapolated to calculate the density of the testing sample. In helium pycnometry method, dry powders of the testing 3-D structure are filled with helium, and the helium pressure produced by a variation of volume is studied to provide for the density. The measured density based on the dry power samples does not reflect the real density of the 3-D structure because of the ultralow density of the 3-D structure, the framework easily collapses during the drying process, hence providing much smaller numbers in the porosity measurement than when the 3-D structure is fully extended, for example, like when the 3-D structure is fully extended in a buffer solution.

In certain embodiments, the density of the 3-D structure can be determined using the dry mass of the 3-D structure divided by the total volume of such 3-D structure in an aqueous solution. For example, dry mass of the core particles with and without the 3-D structure can be determined respectively, and the difference between the two would be the total mass of the 3-D structure. Similarly, the volume of a core particle with and without the 3-D structure in an aqueous solution can be determined respectively, and the difference between the two would be the volume of the 3-D structure on the core particle in an aqueous solution.

In certain embodiments, the porous nanostructure can be dispersed as multiple large nanoparticles coated with the 3-D structure in an aqueous solution, in such case, the total volume of the 3-D structure can be calculated as the average volume of the 3-D structure for an individual large nanoparticle multiplied with the number of the large nanoparticles.

For each individual large nanoparticle, the size (e.g. radius) of the particle with 3-D structure can be determined with Dynamic Light Scattering (DLS) techniques, and the size (e.g. radius) of the particle core without the 3-D structure can be determined under Transmission Electron Microscope (TEM), as the 3-D structure is substantially invisible under TEM. Accordingly, the volume of the 3-D structure on an individual large nanoparticle can be obtained by subtracting the volume of the particle without 3-D structure from the volume of the particle with the 3-D structure.

The number of large nanoparticles for a given core mass can be calculated using any suitable methods. For example, an individual large nanoparticle may be composed of a plurality of small nanoparticles which are visible under TEM. In such case, the average size and volume of a small nanoparticle can be determined based on measurements under TEM, and the average mass of a small nanoparticle can be determined by multiplying the known density of the core material with the volume of the small particle. By dividing the core mass with the average mass of a small nanoparticle, the total number of small nanoparticles can be estimated. For an individual large nanoparticle, the average number of small nanoparticles in it can be determined under TEM. Accordingly, the number of large nanoparticles for a given core mass can be estimated by dividing the total number of small nanoparticles with the average number of small nanoparticels in an individual large nanoparticle.

Alternatively, the low density, porous 3-D structure refers to a structure having 40%-99.9% (preferably 50% to 99.9%) of empty space or pores in the structure, where 80% of the pores having size of 1 nm to 500 nm in pore radius.

The porosity of the 3-D structure can be characterized by the Gas/Vapor adsorption method. In this technique, usually nitrogen, at its boiling point, is adsorbed on the solid sample. The amount of gas adsorbed at a particular partial pressure could be used to calculate the specific surface area of the material through the Brunauer, Emmit and Teller (BET) nitrogen adsorption/desorption equation. The pore sizes are calculated by the Kelvin equation or the modified Kelvin equation, the BJH equation (see, e.g. D. Niu et al., *J. Am. chem. Soc.* 132, 15144-15147 (2010)).

The porosity of the 3-D structure can also be characterized by mercury porosimetry (see, e.g. Varadan V. K. et al., supra). Briefly, gas is evacuated from the 3-D structure, and then the structure is immersed in mercury. As mercury is non-wetting at room temperature, an external pressure is applied to gradually force mercury into the sample. By monitoring the incremental volume of mercury intruded for each applied pressure, the pore size can be calculated based on the Washburn equation.

Figure 2:
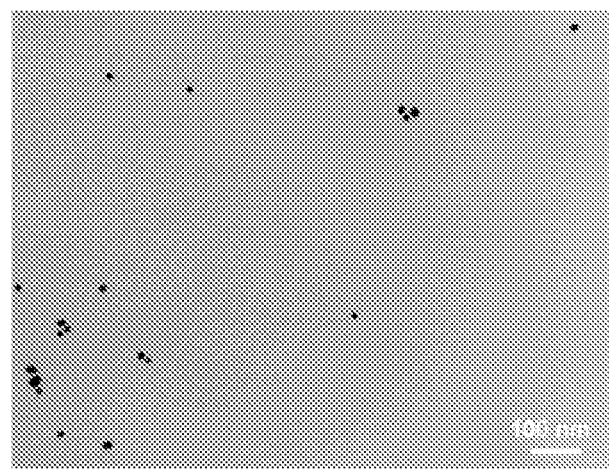
FIG. 2. An exemplary TEM image of silanized Au nanoparticles with core size of Au at ~20 nm and hydrodynamic size ~60 nm. No siliceous coating is visible from the TEM.
Figure 3:
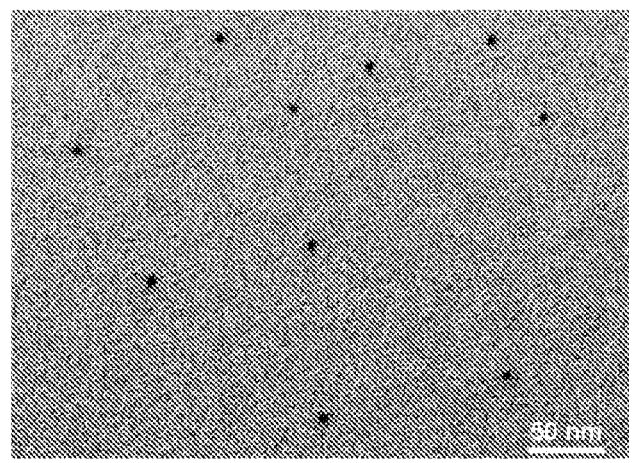
FIG. 3. An exemplary TEM image of silanized quantum dots with nanoparticle core size of ~6 nm and hydrodynamic size ~200 nm. The siliceous coating is not obviously visible from the TEM.
Figure 4:
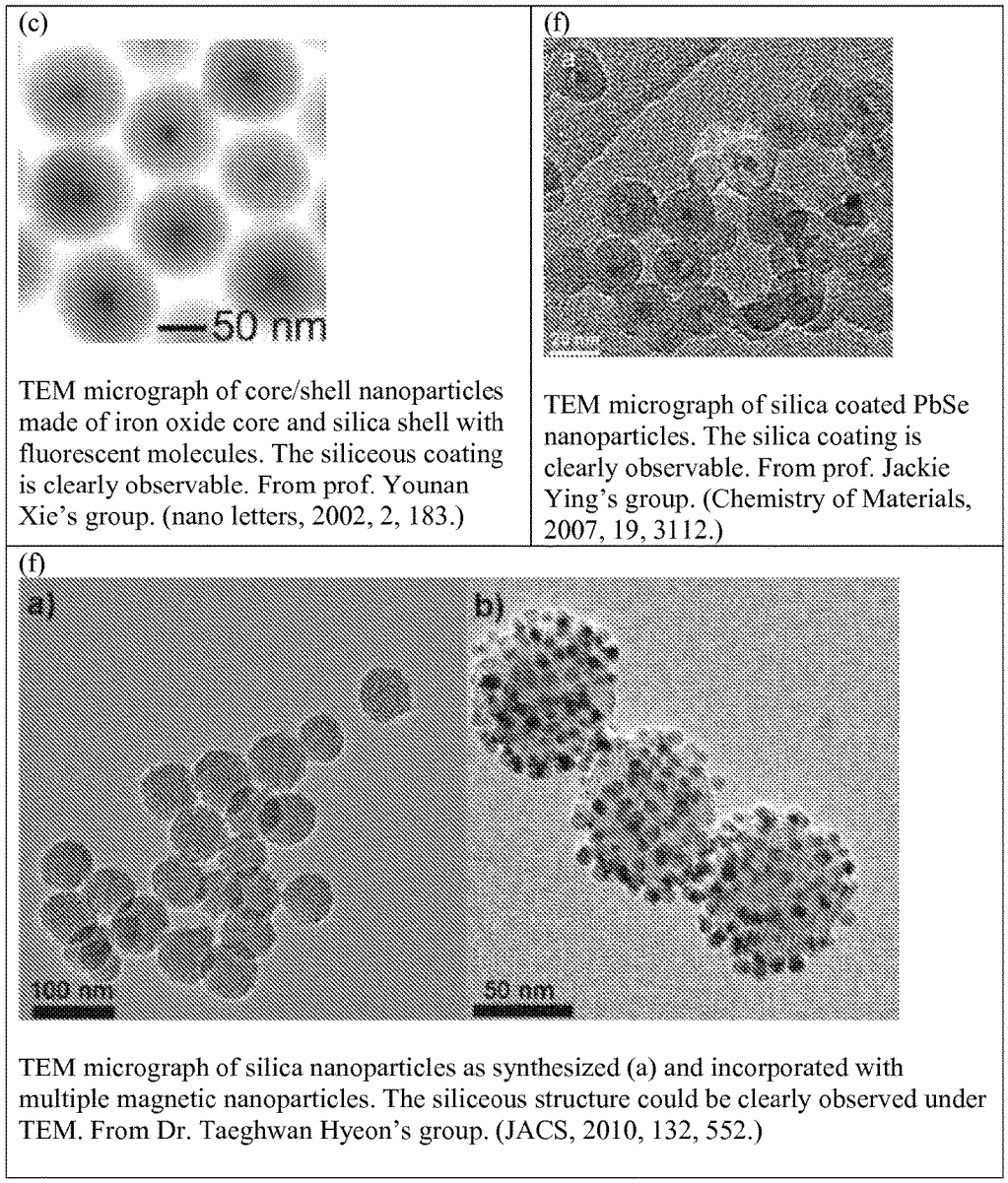
FIG. 4. Exemplary TEM images of coated nanoparticles known in the art, in which the coatings are obviously observable under TEM.

Alternatively, the low density, porous 3-D structure refers to a structure that has a material property, that is, the porous structure (except to the core nanoparticle or core nanoparticles) could not be obviously observed or substantially transparent under transmission electron microscope, for example, even when the feature size of the 3-D structure is in the 10s or 100s nanometer range. The term "obviously observed" or "substantially transparent" as used herein means that, the thickness of the 3-D structure can be readily estimated or determined based on the image of the 3-D structure under TEM. The nanostructure (e.g. nanoparticles coated with or embedded in/on a low density porous 3-D structure) can be observed or measured by ways known in the art. For example, the size (e.g. radius) of the nanostructure with the 3-D structure can be measured using DLS methods, and the size (e.g. radius) of the core particle without the 3-D structure can be measured under TEM. In certain embodiments, the thickness of the 3-D structure is measured as 10s, 100s nanometer range by DLS, but cannot be readily determined under TEM. For example, when the nanostructures provided herein are observed under Transmission Electron Microscope (TEM), the nanoparticles can be identified, however, the low density porous 3-D structure can not be obviously observed, or is almost transparent (e.g., see FIGS. 2 and 3). This distinguishes the nanostructures provided herein from those reported in the art (see, FIG. 4) that comprise nanoparticles coated with crosslinked and size tunable 3-D structure, including the mesoporous silica nanoparticles or coating (see, e.g., J. Kim, et. al., J. Am. Chem. Soc., 2006, 128, 688-689; J. Kim, et. al., Angew. Chem. Int. Ed., 2008, 47, 8438-8441). This feature also indicates that the low density porous 3-D structure provided herein has a much lower density and/or is highly porous in comparison to other coated nanoparticles known in the art.

The porosity of the 3-D structure can be further evaluated by the capacity to load different molecules (see, e.g. Wang L. et al., *Nano Research* 1, 99-115 (2008)). As the 3-D structure provided herein has a low density, it is envisaged that more payload can be associated with the 3-D structure than with other coated nanoparticles (see, e.g. FIG. 1). For example, when 3-D structure is loaded with organic fluorophores such as Rhodamin, over $10^5$ Rhodamin molecules can be loaded to 3-D structure of one nanoparticle.

In certain embodiments, the low density structure refers to a structure capable of absorbing or carrying a fluorescent payload whose fluorescence intensity is at least 100 fold of that of the free fluorescent molecule (e.g. at least 150 fold, 200 fold, 250 fold, 300 fold, 350 fold, 400 fold, 450 fold, 500 fold, 550 fold or 600 fold). The fluorescence intensity of a loaded nanoparticle can be quantified under the same excitation and emission wave lengths as that of the fluorescent molecules. The fluorescence intensity of the loaded low density structure indicates the payload of the fluorescent molecule, and also indirectly reflects the porosity of the low density structure.

In certain embodiments, the low density, porous 3-D structure is made of silane-containing or silane-like molecules (e.g., silanes, organosilanes, alkoxysilanes, silicates and derivatives thereof).

In certain embodiments, the silane-containing molecule comprises an organosilane, which is also known as silane coupling agent. Organosilane has a general formula of $RxSiY_{(4-x)}$, wherein R group is an alkyl, aryl or organofunctional group. Y group is a methoxy, ethoxy or acetoxy group. x is 1, 2 or 3. The R group could render a specific function such as to associate the organosilane molecule with the surface of the core nanoparticle or other payloads through covalent or non-covalent interactions. The Y group is hydrolysable and capable of forming a siloxane bond to crosslink with another organosilane molecule. Exemplary R groups include, without limitation, disulphidealkyl, aminoalkyl, mercaptoalkyl, vinylalkyl, epoxyalkyl, and methacrylalkyl, carboxylalkyl groups. The alkyl group in an R group can be methylene, ethylene, propylene, and etc. Exemplary Y groups include, without limitation, alkoxyl such as $OCH_3$, $OC_2H_5$, and $OC_2H_4OCH_3$. For example, the organosilane can be amino-propyl-trimethoxysilane, mercapto-propyl-trimethoxysilane, carboxyl-propyl-trimethoxysilane, aminopropyl-triethoxysilane, mercapto-propyl-triethoxysilane, carboxyl-propyl-triethoxysilane, Bis-[3-(triethoxysilyl) propyl]-tetrasulfide, Bis-[3-(triethoxysilyl) propyl]-disulfide, aminopropyltriethoxysilane, N-2-(aminoethyl)-3-amino propyltrimethoxysilane, Vinyltrimethoxysilane, Vinyl-tris (2-methoxyethoxy) silane, 3-methacryloxypropyltrimethoxy silane, 2-(3,4-epoxycyclohexy)-ethyl trimethoxysilane, 3-glycidoxy-propyltriethoxysilane, 3-isocyanatopropyltriethoxysilane, and 3-cyanatopropyltriethoxysilane.

The 3-D structure interacts with the core nanoparticles through 1) intra-molecular interaction such as covalent bonds (e.g., Sigma bond, Pi bond, Delta bond, Double bond, Triple bond, Quadruple bond, Quintuple bond, Sextuple bond, 3c-2e, 3c-4-e, 4c-2e, Agostic bond, Bent bond, Dipolar bond, Pi backbond, Conjugation, Hyperconjugation, Aromaticity, Hapticity, and Antibonding), metallic bonds (e.g., chelating interactions with the metal atom in the core nanoparticle), or ionic bonding (cation π-bond and salt bond), and 2) inter-molecular interaction such as hydrogen bond (e.g., Dihydrogen bond, Dihydrogen complex, Low-barrier hydrogen bond, Symmetric hydrogen bond) and non covalent bonds (e.g., hydrophobic, hydrophilic, charge-charge, or π-stacking interactions, van der Waals force, London dispersion force, Mechanical bond, Halogen bond, Aurophilicity, Intercalation, Stacking, Entropic force, and chemical polarity).

Methods of Preparation

Another aspect of the present disclosure relates to methods of forming a nanostructure comprising at least one core nanoparticle with low-density, porous 3-D structure. For example, the nanostructure is formed by coating or surrounding one or more core nanoparticle with low density, porous 3-D structure such that the particle(s) is or are embedded in the 3-D structure.

The low-density, porous 3-D structure is formed by the depositing, or covering of the surface of the core nanoparticle through the assembly or cross-linking of silane-containing or silane-like molecules. The low density porous 3-D structure can be prepared by a silanization process on the surface of the core nanoparticles. Silanization process includes, for example, the steps of crosslinking silicon-containing or silane-like molecules (e.g., alkoxysilanes such as amino-propyl-trimethoxysilane, mercapto-propyl-trimethoxysilane, or sodium silicate) under acidic or basic conditions.

In certain embodiments, an acidic or a basic catalyst is used in the crosslinking. Exemplary acid catalyst include, without limitation, a protonic acid catalyst (e.g. nitric acid, acetic acid and sulphonic acids) and Lewis acid catalyst (e.g. boron trifluoride, boron trifluoride monoethylamine complex, boron trifluoride methanol complex, $FeCl_3$, $AlCl_3$, $ZnCl_2$, and $ZnBr_2$). Exemplary basic catalysts include, an amine or a quaternary ammonium compound such as tetramethyl ammonium hydroxide and ammonia hydroxide.

The silanization process may include one or more stages, for example, a priming stage in which the 3-D structure starts to form, a growth stage in which a layer of siliceous structure is readily formed on the core nanoparticle and more are to be formed, and/or an ending stage in which the 3-D structure is about to be completed (e.g. the outer surface of the 3-D structure is about to be formed). During the silanization process, one or more silane-containing molecules can be added at different stages of the process. For example, in the priming stage, organosilanes such as amino-propyl trimethoxyl silane or mercaptopropyl trimethoxyl silane can be added to initiate the silanization on the core nanoparticle surface. For another example, silane molecules having fewer alkoxy group (e.g. only 2 alkoxy group) can be added to the reaction at the growth stage of silanization. For another example, at the ending stage of silanization, organo silane molecules with one or a variety of different functional groups may be added. These functional groups can be amino, carboxyl, mercapto, or phosphonate group, which can be further conjugated with other molecules, e.g. hydrophilic agent, a biologically active agent, a detectable label, an optical responsive group, electronic responsive group, magnetic responsive group, enzymatic responsive group or pH responsive group, or a binding partner, so as to allow further modification of the 3-D structure in terms of stability, solubility, biological compatibility, capability of being further conjugation or derivation, or affinity to payload. Alternatively, the functional groups can also be a group readily conjugated with other molecules (e.g. a group conjugated with biologically active agent, a thermal responsive molecule, an optical responsive molecule, an electronic responsive molecule, a magnetic responsive molecule, a pH responsive molecule, an enzymatic responsive molecule, a detectable label, or a binding partner such as biotin or avidin).

To control the formation of low density siliceous structure, the preparation further includes density reducing procedures such as introducing air bubbles in the reaction or formation, increasing reaction temperature, microwaving, sonicating, vertexing, labquakering, and/or adjusting the chemical composition of the reaction to adjust the degree of the crosslinking of the silane molecules. Without being bound to theory, it is believed that these procedures can help make the reaction medium homogeneous, well dispersed and promote the formation of low density porous 3-D structure with increased voids or porosity.

In certain embodiments, the density reducing procedure comprises sonicating the reaction or formation mixture. The conditions of the sonicating procedure (e.g. duration) in the silanization process can be properly selected to produce a desired porosity in the resulting low density porous 3-D structure. For example, the sonicating can be applied throughout a certain stage of the silanization process. The duration of sonicating in a silanization stage may last for, e.g. at least 1 hour, 1.5 hours, 2 hours, 2.5 hours, 3 hours, 3.5 hours, 4 hours. In certain embodiments, sonicating is applied in each stage of the silanization process.

In certain embodiments, the density reducing procedures comprise introducing at least one alcohol to the reaction. In certain embodiments, the alcohol has at least 3 (e.g. at least 4, at least 5 or at least 6) carbon atoms. For example, the alcohol may have 3, 4, 5, 6, 7, 8, 9, 10, 11, 12 or more carbon atoms. In certain embodiments, the alcohol can be monohydric alcohols, or polyhydric alcohols. Illustrative examples of monohydric alcohols include, propanol, butanol, pentanol, hexyl alcohol, etc. Illustrative examples of polyhydric alcohols include, propylene glycol, glycerol, threitol, xylitol, etc. In certain embodiments, the alcohol can have a saturated carbon chain or an unsaturated carbon chain. An alcohol having a saturated carbon chain can be represented as $C_nH_{(2n+2)}O$ in chemical formula. In certain embodiments, n is no less than 3, or no less than 4, or no less than 5 (e.g. n=3, 4, 5, 6, 7, 8, 9, 10, 11, 12 or more). Alcohol with an unsaturated carbon chain has a double or a triple bond between two carbon atoms. In certain embodiments, the alcohol can be a cyclic alcohol, for example, cyclohexanol, inositol, or menthol.

In certain embodiments, the alcohol can have a straight carbon chain (e.g. n-propyl alcohol, n-butyl alcohol, n-pentyl alcohol, n-hexyl alcohol, etc) or a branched carbon chain (e.g. isopropyl alcohol, isobutyl alcohol, tert-butyl alcohol, etc). In certain embodiments, the alcohol is present in a volume fraction of about 30% to about 70% (e.g. about 30% to about 70%, about 30% to about 60%, about 30% to about 55%, about 40% to about 70%, about 45% to about 70%, about 40% to about 60%). In certain embodiments, the alcohol is present in volume fraction of around 50% (e.g. around 45%, around 46%, around 47%, around 48%, around 49%, around 50%, around 51%, around 52%, around 53%, around 54%, around 55%, around 56%, around 57%, around 58%, around 59%, or around 60%,).

In certain embodiments, the density reducing procedure comprises introducing air bubbles to the reaction. In certain embodiments, the air bubbles can be in constant presence during the reaction process. The air bubbles can be introduced to the reaction through any suitable methods, for example, by blowing bubbles to the reaction, or by introducing a gas-producing agent to the reaction mixture.

Other experimental conditions can also be optimized to provide for formation of a desired low density porous 3-D structure. Such experimental conditions include, for example, the concentration of the core nanoparticles, the concentration of the catalyst, the ratio of the concentration of the catalyst and the core nanoparticle, the temperature at which the low density siliceous structure is formed, or the molecular structure of the organosilanes.

In certain embodiments, the method further comprises introducing one or more functional groups within in or on the surface of the porous structure. The functional groups may be introduced during the formation of the porous structure during the cross-linking process, for example, by adding silicon-containing compounds containing such functional groups during the cross-linking, in particular, during the ending stage of the cross-linking process. The functional groups may also be introduced after the formation of the cross-linking product, for example, by introducing functional groups to the surface of the cross-linking product by chemical modification. In certain embodiments, the functional groups are inherent in the porous structure.

The functional groups serve as linkage between the porous structure and payloads. Examples of the functional groups include, but are not limited to amino, mercapto, carboxyl, phosphonate, biotin, streptavidin, avidin, hydroxyl, alkyl or other hydrophobic molecules, polyethylene glycol or other hydrophilic molecules, and photo cleavable, thermo cleavable or pH responsive linkers.

In certain embodiments, the method further comprises purifying the obtained nanostructure product. The purification may include use of dialysis, tangential flow filtration, diafiltration, or combinations thereof.

The thickness of the low density porous 3-D structure, which directly correlates to the size of the nanostructure, could be controlled (e.g. from 1 nm to 1000 nm) by, for example, modifying the quantity of the silane-containing molecules (e.g. trialkoxysilane or sodium silicate), the reaction time, and time lapse between reaction steps and such kind of reaction parameters.

The thickness of the 3-D structure can be about 1 to 5 nm thick. In certain embodiments, the thickness can be about 1 to 10 nm thick. In certain embodiments, the thickness can be about 1 to 20 nm thick. In certain embodiments, the thickness can be about 1 to 30 nm thick. In certain embodiments, the thickness can be about 1 to 40 nm thick. In certain embodiments, the thickness can be about 1 to 50 nm thick. In certain embodiments, the thickness can be about 1 to 60 nm thick. In certain embodiments, the thickness can be about 1 to 100 nm thick. In certain embodiments, the thickness can be about 1 to 500 nm thick. In certain embodiments, the thickness can be about 1 to 1000 nm thick.

After the low-density, porous 3-D structure is formed on the surface of the core nanoparticle, the core nanoparticle is embedded in the 3-D structure. The resulting nanostructure can have a thickness (e.g., the longest dimension of the nanostructure or a diameter if the structure is a sphere) of about 1 to 1000 nm, 1 to 100 nm, or 1 to 10 nm. In another embodiment, the nanostructure can have a diameter of about 1 to 30 nm. In another embodiment, the nanostructure can have a diameter of about 500 nm. In another embodiment, the nanostructure can have a diameter of about 100 nm. In another embodiment, the nanostructure can have a diameter of about 50 nm. In another embodiment, the nanostructure can have a diameter of about 30 nm. In another embodiment, the nanostructure can have a diameter of about 10 nm.

Payloads

In certain embodiments, the nanostructures provided herein carry or are associated with a payload. The payloads to be carried or associated with the nanostructure include, but are not limited to, a detectable agent, a targeting moiety, a binding partner, a biological active agent, a drug, a therapeutic agent, a radiological agent, a chemological agent, a small molecule drug, a biological drug (e.g., peptides, proteins, antibodies, antigens, nucleic acids, aptamers, and the like) and combinations thereof, which can be used to image, detect, study, monitor, evaluate, screen, and/or a disease, condition, or related biological event. Payloads may be physically absorbed into the porous structure or linked to the porous structure through functional groups disclosed herein.

A detectable agent can be a fluorescent molecule, a chemo-luminescent molecule, a bio-luminescent molecule, a radioisotope, a MRI contrast agent, a CT contrast agent, an enzyme-substrate label, and/or a coloring agent etc. Examples of fluorescent molecules include, without limitation, fluorescent compounds (fluorophores) which can include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies); Alexa® Fluor 350; Alexa® Fluor 405; Alexa® Fluor 500; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate;

Beta Lactamase; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (nonratio); DiA (4-Di-16-ASP); Dichlorodihydrofluorescein Diacetate (DCFH); DiD-Lipophilic Tracer; DiD (DiIC18 (5)); DIDS; Dihydrorhodamine 123 (DHR); DiI (DiIC18 (3)); Dinitrophenol; DiO (DiOC18(3)); DiR; DiR (DiIC18 (7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PYMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), fluorescent semiconductor nanoparticles, lanthanides or combinations thereof.

Examples of radioisotopes include, $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, $^{32}P$, $^{18}F$, $^{201}Tl$, $^{67}Ga$, $^{137}Cs$ and other radioisotopes.

Examples of enzyme-substrate labels include, luciferases (e.g., firefly luciferase and bacterial luciferase), luciferin, 2,3-dihydrophthalazinedionesm, alate dehydrogenase, urease, peroxidase such as horseradish peroxidase (HRPO), alkaline phosphatase, -galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

A targeting moiety has affinity to an interested target (e.g., a cell, a cellular component, a tissue, a protein, an antibody, an antigen, a DNA, a RNA and the like). Examples of a targeting moiety include, antibodies (e.g. antibodies to tumor surface antigens, antibodies to cell-specific antigens, or antibodies to receptors), a ligand to a receptor (e.g. growth factors, hormones, cytokines, or neurotransmitters), aptamers, peptides, antigens, nucleic acids, polynucleotides, polysaccharides, sugars, fatty acids, steroids, purines, pyrimidines, a hapten or combinations thereof.

Examples of a binding partner include, antibodies, antigens, receptors, ligands, DNA, RNA, peptide, aptamer, biotin, avidin, strepavidin, lectin, carbohydrate, Protein A, antibody Fc, desthiobiotin, and iminobiotin.

Examples of a biologically active agent include, therapeutic agents, proteins, antibodies, peptides, nucleic acids, enzymes, thermal-responsive molecules, optical-responsive molecules, electronic-responsive molecules, magnetic-responsive molecules, pH-responsive molecules, enzymatic responsive molecules and/or chemical compounds. Exemplary of therapeutic agents include, without limitation, local anesthetics, antiepileptic drugs and anticonvulsants, anti-alzheimer's disease drugs, analgesics, antipodaghc, antihypertensive drugs, antiarrhythmic drugs, diuretic drugs, drugs for treating liver diseases, drugs for treating pancreatic diseases, antihistamine drugs, anti-allergic drugs, glucocorticoid drugs, sex hormone drugs and contraceptive drugs, hypoglycemic drugs, anti-osteoporosis drugs, antibiotics, sulfonamides, quinolones, and other synthetic antibacterial drugs, antituberculous drugs, antiviral drugs, anti-neoplasm drugs, and immunomodulators.

With respect to antigens or antibodies thereof, a protein of interest can be any one or more of the following antigens including but not limited to: 1) leukocyte markers, such as CD2, CD3, CD4, CD5, CD6, CD7, CD8, CD11a,b,c, CD13, CD14, CD18, CD19, CD20, CD22, CD23, CD27 and its ligand, CD28 and its ligands B7.1, B7.2, B7.3, CD29 and its ligand, CD30 and its ligand, CD40 and its ligand gp39, CD44, CD45 and isoforms, CDw52 (Campath antigen), CD56, CD58, CD69, CD72, CTLA-4, LFA-1 and TCR; 2) histocompatibility antigens, such as MHC class I or II, the Lewis Y antigens, SLex, SLey, SLea, and SLeb; 3) integrins, such as VLA-1, VLA-2, VLA-3, VLA-4, VLA-5, VLA-6, and LFA-1; 4) adhesion molecules, such as Mac-1 and p150, 95; 5) selectins, such as L-selectin, P-selectin, and E-selectin and their counterreceptors VCAM-1, ICAM-1, ICAM-2, and LFA-3; 6) interleukins, such as IL-1, IL-2, IL-3, IL-4, IL-5, IL-6, IL-7, IL-8, IL-10, IL-11, IL-12, IL-13, IL-14; and IL-15; 7) interleukin receptors, such as IL-1R, IL-2R, IL-4R, IL-5R, IL-6R, IL-7R, IL-8R, IL-10R, IL-11R, IL-12R, IL-13R, IL-14R, and IL-15R; 8) chemokines, such as PF4, RANTES, MIP1.alpha., MCP1, NAP-2, Grou, Grog, and IL-8; 9) growth factors, such as TNFalpha, TGFbeta, TSH, VEGF/VPF, PTHrP, EGF family, FGF, PDGF family, endothelin, and gastrin releasing peptide (GRP); 10) growth factor receptors, such as TNFalphaR, RGFbetaR, TSHR, VEGFR/VPFR, FGFR, EGFR, PTHrPR, PDGFR family, EPO-R, GCSF-R and other hematopoietic receptors; 11) interferon receptors, such as IFN.alpha.R, IFN.beta.R, and IFN.gamma R; 12) Igs and their receptors, such as IgE, FceRI, and FCeRII; 13) tumor antigens, such as her2-neu, mucin, CEA and endosialin; 14) allergens, such as house dust mite antigen, lol pl (grass) antigens, and urushiol; 15) viral proteins, such as CMV glycoproteins B, H, and gCIII, HIV-1 envelope glycoproteins, RSV envelope glycoproteins, HSV envelope glycoproteins, EBV envelope glycoproteins, VZV envelope glycoproteins, HPV envelope glycoproteins, Hepatitis family surface antigens; 16) toxins, such as pseudomonas endotoxin and osteopontin/uropontin, snake venom, and bee venom; 17) blood factors, such as complement C3b, complement C5a, complement C5b-9, Rh factor, fibrinogen, fibrin, and myelin associated growth inhibitor; 18) enzymes, such as cholesterol ester transfer protein, membrane bound matrix metalloproteases, and glutamic acid decarboxylase (GAD); and 19) miscellaneous antigens including ganglioside GD3, ganglioside GM2, LMP1, LMP2, eosinophil major basic protein, eosinophil cationic protein, PANCA, Amadori protein, Type IV collagen, glycated lipids, .gamma.-interferon, A7, P-glycoprotein and Fas (AFO-1) and oxidized-LDL.

In certain embodiments, a protein of interest can be antibodies or fragments thereof which bind to an antigen (non-limiting example of antigens are shown as above). The antibodies or fragments can be polyclonal, monoclonal, of animal origin (e.g., murine, rabbit, camel), of human origin (e.g., fully human), chimeric, humanized, variable regions, CDRs, ScFv, bispecific, diabody, or other forms of antibodies with antigen-binding capabilities The payload may be introduced during or after the formation of the nanostructures. For example, when the nanostructure is formed through silanization process, the payload (e.g. a fluorescent compound) can be introduced to the silanization system, so as to allow the incorporation of the payload into the nanostructure during the silanization process. For another example, the payload may be mixed with the readily formed nanostructure, e.g. in solution, dispersion, suspension, emulsion etc, to allow incorporation of the payload to the porous compartment of the nanostructure, or to allow conjugation of the payload to the functional groups on the nanostructure.

In certain embodiment, at least one payload can be associated with the porous structure. For example, only one group of homogenous payloads are associated with the porous structure. For another example, the first payload and the second payload are associated with the porous structure. While both payloads are selected from the groups consisting of a detectable agent, a targeting moiety, a binding partner, a biological active agent, a drug, a therapeutic agent, a radiological agent, a chemological agent, a small molecule drug, a biological drug (e.g., peptides, proteins, antibodies, antigens, nucleic acids, aptamers, and the like); the first payload is not the same as the second payload. For instance, the first payload is a targeting agent that lead the nanostructure to specifically binds to or be associated with a target (e.g., a cancer cell), and the second payload is a detectable gent (for diagnosis) or a therapeutic agent (for treatment).

In certain embodiments, the first payload is associated with the porous structure in one area of the structure and the second payload is associated with the porous structure in another area of the structure so that the nanostructure can be directional or oriented with respect to the distribution of payloads in the nanostructure. Such site selective modification could be achieved by depositing the porous structure on a substrate, then partially coating the substrate with a protective polymer layer, such as poly(3-hexyl-thiophene) (P3HT) and poly(methyl methacrylate) that could be dissolved using certain solvents such as chloroform or pyridine after the site selective modification is finished. (Liu H., et. al., nano letters, 2004, vol 4., 2397-2401). A second modification could be achieved after the protective layer is removed and the unmodified nanostructure is exposed and further modified with different payloads. Further, the nanostructure could be deposited on the substrate with bonding through cleavable molecules, for example, photo cleavable molecules such as photocleavable biotin amine reactive labeling reagents (www.ambergen.com), then the nanostructure could be released after site selective modifications. In addition, with cleavable linker molecule bound to the substrate, the nanostructures could be released after the first site selective modification (SSM1). SSM1 could include both functional groups for linking the SSM1 modified area to a substrate in the next site selective modification step and payloads for signal generating, drugs or other functional purposes. The procedure could be repeated for SSM2. By controlling the protective polymer layer thickness, 3rd, 4th or more site selective modification steps could be carried out to render the nanostructures multiple regions of different payloads.

Products by Process

Another aspect of the present disclosure relates to nanostructures prepared by any of the methods provided herein. The nanostructures prepared herein may be optionally isolated, purified, dried, or associated with one or more payloads, using methods described herein and/or conventional methods known in the art. The nanostructures prepared in the present disclosure can be further characterized for the 3-D structure, such as density, porosity, surface areas, thickness etc. of the 3-D structure. Optionally, the payloads may be characterized as well, such as the amount of the payload or the detectable signal of the payload.

Methods of Use

In certain embodiments, the nanostructure provided herein can be used in the manufacture of therapeutic or diagnostic compositions.

In certain embodiments, the nanostructure may be used to deliver one or more therapeutic agents. For example, the nanostructure may be used to provide for desired delivery (e.g. targeted delivery) and/or desired release (e.g. extended and/or controlled release) of the therapeutic agent(s). The nanostructure may be delivered to a subject via a suitable route (e.g., intravenous, intraperitoneal, intramuscular, intradermal, subcutaneous, transdermal, subdermal, intracranial, intranasal, mucosal, anal, vaginal, oral, sublingual, buccal, or nasal). The nanostructure suitable for therapeutic use may comprise one or more therapeutic agent, either as an associated payload, or as a conjugated molecule (e.g. a prodrug). Optionally, for target delivery, the nanostructure may further comprise a targeting moiety.

The nanostructure may also be used on samples (e.g. in vitro or ex vivo) for diagnostic use. For example, the nanostructure may be applied to or contacted with a sample under a suitable condition that allows an expected reaction (e.g. hybridization, amplification, affinity binding, staining, etc.) with its target molecule suspected of being present in the sample (e.g. a biomarker for a condition, a marker antigen, a pathogen, and/or a virus gene sequence). The presence and/or extent of the reaction may be detected or measured, so as to provide for information of presence or absence of the target molecule, and/or the amount (e.g. concentration) of such target molecule. The nanostructures useful in such diagnostic use may comprise an agent capable of reacting with the interested target molecule. Such agent can be a binding partner such as antibody, antigen, aptamer, nucleic acid, probe, chemical or other suitable agents. Such agent may be associated with the nanostructure as a payload and/or be conjugated to the nanostructure. Optionally, the nanostructure may further comprise a detectable label that allows detection of the reaction.

In certain embodiments, the nanostructure provided herein can be used in the manufacture of reagents useful in a qualitative or quantitative test. For example, the nanostructure may be used to contact an analyte and to allow identification and/or quantification of the analyte. The analyte may be any substance that can be detected, such as chemicals, explosives (e.g. TNT), drugs (e.g. cocaine, heroin, cannabis, etc.), hazardous substances, metal ions (e.g. heavy metal ions), contaminants, organic compounds, alcohol, anabolic steroids, protons, nitric monoxide, blood sugar, and metabolites etc. The analyte may be in any suitable sample form, such as for example, in a biological specimen (e.g. urine, sweat, breath, hair, saliva, and blood), in an environmental specimen (e.g. river water, soil, and air), or in a lab sample (e.g. dissolved in a lab buffer). The nanostructure suitable for such analytic use may comprise a detecting agent (e.g. as a payload or as a conjugate molecule) that allows identification and/or quantification of the analyte, and such detecting agent can be appropriately selected by people in the art based on the known detection methods for the analyte.

In certain embodiments, the nanostructure provided herein can be used in the manufacture of reagents useful in molecular imaging. For example, the nanostructure provided herein may be administered in vivo or in vitro to a subject (e.g., a mammal, a human or other animals) via a suitable route (e.g. intravenously, intra-arterially, orally, dermal application, subcutaneously, intramuscular, intraperitoneal), followed by image generation of the subject using a suitable device, such as an X-ray device, an MRI device, a CT device, or devices for optical imaging, optical coherence tomography, computed tomography, or positron emission tomography. The generated images may be further analyzed to provide distribution of the administered nanostructures in the subject, or in an interested tissue, organ or compartment of the subject. The nanostructure useful in molecular imaging may carry or be associated with a payload comprising a fluorescent molecule, a bioluminescent molecule, a radio isotope and/or other agents as a suitable imaging or contract agent (A review on molecular imaging can be found at: Weissleder, R. et al, Radiology, 219: 316-333 (2001)).

In certain embodiments, the nanostructure provided herein can be used in the manufacture of reagents useful in separation, purification or enrichment. For example, the nanostructure may be used to contact a mixture which contains a component for which a separation/purification/enrichment is interested. The interested component may be, for example, a cell (e.g. tumor cell, a cell expressing a specific marker antigen), a protein (e.g. antibody, antibody fragment, antigen etc.), a nucleic acid, and a chemical compound etc. The mixture may be or be derived from, for example, a biological specimen (e.g. blood, serum, plasma, urine, tissue, cell extract, cell lysate), a synthesized chemical product, an extract of herbs or plants, and etc. The nanostructure comprises one or more capturing agents that have an affinity to the interested component. For example, the nanostructure may carry or be conjugated with, for example, an antigen, antibody, complementary nucleic acid, aptamer, and any other suitable binding partners. The nanostructure with the interested component captured thereon, may be separated from the remnants of the mixture using any suitable separation methods, such as for example, by filtration, centrifugation, chromatography (e.g. size-exclusion chromatography), application of magnetic field (e.g. for nanostructures comprising magnetic nanoparticles), or application of electrical field. Optionally, the capture of the interested component by the nanostructure is reversible, so that the component may be released from the nanostructure after the separation/purification/enrichment.

In certain embodiments, the nanostructure provided herein can be used in the manufacture of semiconductors. Such semiconductors may be used in light emitting devices, optoelectronic devices, fluorescent label, electrodes, photovoltaic cells, optical sensors, and biosensors etc. Some of these applications are described in detail in Schmid, G. et al., Nanoparticles: From Theory to Application, published by John Wiley & Sons, 2011.

Delivery into a Biological Sample

Another aspect of the present disclosure relates to uses of the porous nanostructures as disclosed herein in delivering payloads onto or into biological samples.

In certain embodiments, methods are provided for delivering at least one payload unto or into a biological sample, comprising contacting a biological sample with a payload carrying porous nanostructures as provided herein.

The biological sample in the present disclosure includes a cell, a cluster of cells, a tissue, an organ, a biological body from a biological organism. The biological sample can be normal, healthy sample or abnormal, diseased sample (e.g., cancer or tumor).

A biological organism includes, for example, a microorganism (e.g., bacteria), a fungus, a plant and an animal (e.g., a human).

An organ from an animal biological organism (e.g., human) includes, for example, a circulatory organ (e.g., heart, blood and blood vessels), a digestive organ (e.g., salivary glands, esophagus, stomach, liver, gallbladder, pancreas, intestines, rectum and anus), an endocrine organ (e.g., endocrine glands such as the hypothalamus, pituitary or pituitary gland, pineal body or pineal gland, thyroid, parathyroids and adrenals, i.e., adrenal glands), an integumentary organ (e.g., skin, hair and nails), a lymphatic organ (e.g., lymph nodes and vessels, tonsils, adenoids, thymus and spleen), a muscular organ (e.g., muscles), a nervous organ (e.g., brain, spinal cord, peripheral nerves and nerves), a reproductive organ (e.g., ovaries, fallopian tubes, uterus, vagina, mammary glands, testes, vas deferens, seminal vesicles, prostate and penis), a respiratory organ (e.g., the pharynx, larynx, trachea, bronchi, lungs and diaphragm), a skeletal organ (e.g., bones, cartilage, ligaments and tendons), a urinary system (e.g., kidneys, ureters, bladder and urethra). An organ can be normal or healthy, and alternatively, abnormal or unhealthy (e.g., cancerous).

An organ from a plant biological organism includes, for example, root, stem, leaf, flower, seed and fruit.

A tissue from a biological sample (e.g. an animal) includes a connective tissue, a muscle tissue, a nervous tissue, and an epithelial tissue. A tissue can be normal or healthy, and alternatively, abnormal or unhealthy (e.g., cancerous). A tissue from a biological sample (e.g. a plant) includes an epidermis, a vascular tissue and a ground tissue.

A cell can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ (e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell); a cell from an endocrine system or organ (e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte)); a cell from a nervous system or organ (e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph)); a cell from a respiratory system or organ (e.g., a pneumocyte (a type I pneumocyte and a type II pneumocyte), a clara cell, a goblet cell, an alveolar macrophage); a cell from circular system or organ (e.g., myocardiocyte and pericyte); a cell from digestive system or organ (e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, a liver cell (e.g., a hepatocyte and Kupffer cell)); a cell from integumentary system or organ (e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell)), a muscle cell (e.g., myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula densa cell), and a cell from reproductive system or organ (e.g., a spermatozoon, a sertoli cell, a leydig cell, an ovum, an oocyte). A cell can be normal, healthy cell; or a diseased or unhealthy cell (e.g., a cancer cell).

A cell further includes a mammalian stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and an unipotent stem cell (See, Hans R. Schöler (2007). "The Potential of Stem Cells: An Inventory" in Nikolaus Knoepffler, Dagmar Schipanski, and Stefan Lorenz Sorgner. Humanbiotechnology as Social Challenge. Ashgate Publishing, Ltd. pp. 28), any of which may be induced from a somatic cell. A stem cell may also include a cancer stem cell.

In certain embodiments, the porous nanostructure can be used to deliver one or more payloads in vitro to a biological sample (such as a cell culture, or a tissue culture). For example, the porous nanostructure associated with a payload can be introduced into an in vitro biological sample, and the sample can be cultivated under a condition that allows the delivery of the payload to the biological sample.

In certain embodiments, the porous nanostructure can be used to deliver one or more payloads in vivo to a biological sample (such as a cell, a tissue, an organ in a biological organism). For example, the porous nanostructure associated with a payload can be administered to a biological organism via a suitable route such as for example, parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes. The porous nanostructures can be formulated in a suitable dosage form to allow delivery via the administration route, for example, in an injection dosage for parenteral route delivery, and in a solid dosage form, a solution, an emulsion for oral delivery, and in a lotion or cream for a topical delivery. The porous nanostructures can be administered in vivo systematically or locally to a biological sample.

The delivery of the payloads can be measured by any suitable methods. For example, the porous nanostructures or the payload may comprise a detectable label (e.g. fluorescent molecule) which allows for direct observation or detection (e.g. fluorescence imaging) of the porous nanostructures or the payload on or inside the biological sample intended for the delivery. For another example, the payload may comprise a pharmaceutical agent, and to indirectly characterize the delivery of the payload, one can measure the biological effects of payload on the biological sample, the concentration of the pharmaceutical agent in the biological sample, and/or the metabolite or product of the pharmaceutical agent.

In certain embodiments, the porous nanostructure has magnetic property so as to enhance the delivery using magnetic interaction. Such nanostructure can comprise one or a cluster of SIPO nanoparticles as core nanoparticles. The magnetic nanostructures can be attracted to or magnetically guided to a target site when subject to a strong magnetic field, for example a magnetic field from high-filed and/or high-gradient magnets. Methods of using magnetic fields in delivering nanoparticles are well-known in the art, see, for example, McBain, S. C. et al, Int, J. Nanomedicine, 3(2): 169-180 (2008); Polyak, B. et al, Proc Natl Acad Sci U.S.A. 104(2): 698-703 (2008); Urs O. Hafeli et al, Nanoparticulates as Drug Carriers, edited by V. P. Torchilin, Chapter 18, published by Imperial College Press, 2006; Barnett, B. P. et al, Nat. Med., 13, 986-991 (2007); Namiki, Y. et al, Nat. Nanotechnol. 2009, 4, 598-606.

By guiding the magnetic porous nanostructures through the magnetic field, one or more payloads associated with the nanostructure can be directed and delivered to the target site, where they may exhibit the intended biological activities. Such targeted delivery of the payloads can lead to increased payloads at the target site. In certain embodiments, the delivery of the payloads with magnetic porous nanostructure in the presence of a magnetic filed can be at least 5% more (e.g. 10%, 20%, 30%, 40%, 50%, 60%, 70%, 80%, 90%, 100%, or even higher) than the delivery of payloads with a nonmagnetic porous nanostructures or in the absence of a magnetic filed.

In certain embodiments, the size of the porous nanostructure is tailored from 1 nm to 1000 nm to optimize its delivery function. For example, the size of the porous nanostructure is from 1 nm to 10 nm, from 1 nm to 50 nm, from 1 nm to 100 nm, from 1 nm to 200 nm, from 1 nm to 300 nm, from 1 nm to 400 nm, from 1 nm to 500 nm, from 100 nm to 600 nm, from 100 nm to 700 nm, from 100 nm to 800 nm, from 100 nm to 900 nm, or from 100 nm to 1000 nm.

In certain embodiments, the charge of the porous nanostructure is tuned to optimize its delivery function. The porous nanostructure can be tuned to be negatively charged, positively charged or neutral, depending on the requirement or preference of the payload. For example, when delivering DNA which contains negatively charged phosphate groups, a positively charged porous nanostructure may be desirable. Charges on the porous nanostructure can be tuned by performing surface modifications on the porous nanostructure, for example, introducing positive charged groups such as amine groups, negative charged groups such as carboxylic groups, and neutral groups such as methyl (see, for example, Chen L. et al, Nanotechnology, 22(10): 105708 (2011)).

In certain embodiments, the porous nanostructure is biocompatible. The term "biocompatible" means not toxic to the biological sample or biological organism, for example, being physiologically acceptable to the biological sample and not imparting undesirable toxicological effects.

In certain embodiments, the payload is released into the biological sample via electrostatic principals, biological or enzymatic interactions, or through photo, pH, thermal, or electronic sensitive bonds.

Another aspect of the present disclosure relates to the uses of payload-carrying porous nanostructures in delivering payloads onto or cross a biological barrier of a biological sample.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a layer of cells, a biological structure, an inner surface of subjects, organisms, organs or body cavities, an external surface of subjects, organisms, organs or body cavities, or any combination or plurality thereof.

Examples of biological membrane include a lipid bilayer structure, eukaryotic cell membrane, prokaryotic cell membrane, intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies. An organelle envelope may have more than two membranes.

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of cell layer of layer of cells include lining of eukaryotic cells (e.g., epithelium, lamina propria and smooth muscle or muscularis mucosa (in gastrointestinal tract), lining of prokaryotic cells (e.g., surface layer or S-layer which refers to a two dimensional structure monomolecular layer composed of identical proteins or glycoproteins. Specifically, an S-layer refers to a part of the cell envelope commonly found in bacteria and archaea), a biofilm (a structured community of microorganisms encapsulated within a self-developed polymeric matrix and adherent to a living or inert surface), plant cell layer (e.g., empidermis).

Examples of biological structures include structures sealed by tight or occluding junctions which provide a barrier to the entry of toxins, bacteria and viruses from the hostile exterior, e.g. the blood milk barrier and the blood brain barrier (BBB). In particular, BBB is composed of impermeable class of endothelium, which presents both a physical barrier through tight junctions adjoining neighboring endothelial cells and a transport barrier comprised of efflux transporters. BBB is a formidable barrier, e.g., to toxins as well as drugs for neurological disease treatment.

Examples of inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of external surface of subjects, organisms, organs or body cavities include capillaries (e.g. capillaries in the heart tissue), mucous membranes that are continuous with skin (e.g. such as at the nostrils, the lips, the ears, the genital area, and the anus) outer surface of an organ (e.g. liver, lung, stomach, brain, kidney, heart, ear, eye, nose, mouth, tongue, colon, pancreas, gallbladder, duodenum, rectum), skin, cuticle (e.g., dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), or a combination or plurality thereof.

Another aspect of the present disclosure relates to the uses of payload-carrying porous nanostructures in delivering payloads into a target site in a subject. In certain embodiments, the payload-carrying nanostructure is administered into a subject, and attracted to the target site in the presence of an applied magnetic field.

The term "subject" include any living organism, for example, an animal (e.g human, mouse, rat, dog, monkey, pig, cow, sheep, and etc.) and a plant (e.g., rice, wheat, soybean, maize, grain, fruits, tobacco, flowers, and etc.).

The payload-carrying porous nanostructures can be administered to the subject in a suitable route as mentioned above. The nanostructures can be systematically administered (e.g. intravenous injection) or locally administered (e.g. topical application or subcutaneous injection).

In certain embodiments, the target site is a site located at a suitable depth from the body surface such that magnetic targeting can be achieved.

At least one payload can be associated with the porous structure. For example, only one group of homogenous payloads is associated with the porous structure. For another example, the first payload and the second payload are associated with the porous structure. While both payloads are selected from the groups consisting of a detectable agent, a targeting moiety, a binding partner, a biological active agent, a drug, a therapeutic agent, a radiological agent, a chemological agent, a small molecule drug, a biological drug (e.g., peptides, proteins, antibodies, antigens, nucleic acids, aptamers, and the like); the first payload is not the same as the second payload. For instance, the first payload is a targeting agent that lead the nanostructure to specifically binds to or be associated with a target (e.g., a cancer cell), and the second payload is a detectable agent (for diagnosis) or a therapeutic agent (for treatment).

A plurality of payloads can be distributed or oriented in different regions of the nanostructures. For example, the first payload is associated with the porous structure in one area of the structure and the second payload is associated with the porous structure in another area of the structure so that the nanostructure can be directional or oriented with respect to the distribution of payloads in the nanostructure.

For another example, the first payload is a targeting moiety or a binding partner to a biological sample or a biological barrier and the second payload (and a third payload and so on) is a detectable agent, a biological active agent, a drug, a therapeutic agent, a radiological agent, a chemological agent, a small molecule drug, a biological drug (e.g., peptides, proteins, antibodies, antigens, nucleic acids, aptamers, and the like) and combinations thereof. A resulting nanostructures are capable of targeting a biological sample (or a biological barrier) that the first payload specifically binds to and delivering the second payload specifically onto or into the sample or onto or cross the biological barrier. Consequently, the presence of the biological sample can be detected and/or the status of the sample can be modified (e.g., changing from diseased status to a healthy status, changing from un-differentiation to differentiation or leading some biological events in the sample (proliferation, apoptosis, differentiation, and de-differentiation).

Another aspect of the present disclosure relates to a composition comprising a payload carrying nanostructure and a biological sample. In certain embodiments, the payload-carrying nanostructure has been delivered into or onto the biological sample. In certain embodiments, the payload is selected from the group consisting of a targeting moiety, a binding partner, a detectable agent, a biological active agent, a drug, a therapeutic agent, a radiological agent, a chemological agent, a small molecule drug, a biological drug and any combination thereof. In certain embodiments, the biological sample is a cell, a tissue, an organ, or an animal

EXAMPLES

Example 1

Preparation of Nanoparticles of Gold and Semiconductor Quantum Dots with the Low Density Siliceous Structure The low density siliceous structure is a versatile and flexible platform for making biocompatible nanoparticles. For example, to incorporate gold nanoparticles into the siliceous structure, Au nanoparticles synthesized in either water solution or organic solutions could be utilized. Briefly, Au was precipitated out at the sample vial bottom after centrifuge at 13k rpm for 15 min, then silane molecules such as aminopropyltrimethoxysilane and TMAOH was added. The reaction solvent was adjusted using a higher number alcohol, such as butanol or proponol. Then the sample was sonicated for a few hours with constant blowing of air bubbles, afterwards, PEG-silane, mercaptopropyltrimethoxysilane and aminopropyltrimethoxysilane were added, the sample was sonicated for additional 2-3 hours. Afterwards, mixture of chlorotrimethylsilane, methanol, and TMAOH or other silane molecules that only have one alkoxyl group connecting with the silicon atom were added to react with surface siloxyl groups presented on the surface of the already grown siliceous structure. After additional sonicating and aging, stable nanoparticles with the highly porous siliceous structure were collected and stored within physiological buffer solutions through centrifugal filtering, centrifugation, dialysis or any other solution exchange methods. The resulting Au nanostructure was observed under TEM, and an exemplary TEM image was shown in FIG. 2. The nanoparticle core size was about 20 nm and hydrodynamic size was about 60 nm. The siliceous coating was not obvious from the TEM.

Example 2

Preparation of Nanoparticles of Semiconductor Quantum Dots with the Low Density Siliceous Structure As another example, semiconductor quantum dots in the form of individual nanocrystal or nanocrystal clusters could also be incorporated within the highly porous/low density siliceous structure. For example, CdSe/ZnS nanoparticles in organic solvents such as chloroform, Toluene, or Hexane could be precipitated out by adding methanol and then through centrifugation. The nanocrystal pellet was then re-dispersed in aminopropyltrimethoxysilane or mercaptopropyltrimethoxysilane. Afterwards, tetramethyl ammonium hydroxide was added. Then the reaction solvent was adjusted using a higher number alcohol, such as butanol or proponol. After sonicating the sample for 1-4 hours and blowing air bubbles, small amount of aminopropyltrimethoxysilane, mercaptopropyltrimethoxysilane, polyethyleneoxidesilane and water was subsequently added, and the sample then underwent sonication for another 1 to 4 hours. Then, mixture of chlorotrimethylsilane, methanol, and TMAOH or other silane molecules that only have one alkoxyl group connecting with the silicon atom were added. This sample was then sonicated for another 1-4 hours, followed by overnight aging under mild shaking or vibration. The resulting nanoparticles with low density/highly porous siliceous structure were transferred into physiological buffer solutions by centrifugal filtering, centrifugation, dialysis or any other solution exchange methods. The resulting CdSe/ZnS nanostructure was observed under TEM, and an exemplary TEM image was shown in FIG. 3. The nanoparticle core size was about 10 nm and hydrodynamic size was about 200 nm. The siliceous coating was not obvious from the TEM.

Example 3

Preparation and Characterization of Low Density Magnetic Particles

Figure 5:
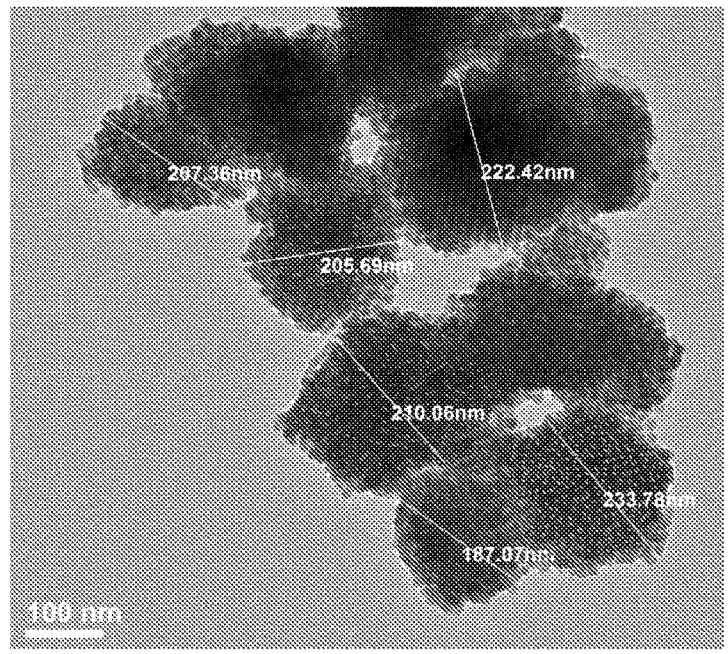
FIG. 5. An exemplary TEM image of LDNS, in which the diameters of the large core nanoparicles are shown.

Preparation of the Magnetic Porous Nanostructure:

Magnetic particles formed by clustering multiple small particles and then being coated were prepared. The clustering happened with the addition of a worse solvent for generating dispersed nanoparticles, such as butanol or isopropanol, followed by the addition of the silanization reagents to form the porous nanostructure under constant blowing of air bubbles. The magnetic porous nanostructure as prepared was observed under TEM (FIG. 5). As shown in FIG. 5, each large core nanoparticle comprised a cluster of small nanoparticles, and the coating was substantially invisible under TEM.

Characterization of Density of the Coating:

To calculate the density of the coating, both the dry mass and the volume of the coating were characterized.

Since the magnetic particles had high magnetic response that they could be directly captured using a magnet. This allowed generation of dry particles to measure the mass of the material. The dry mass of particles before and after coating was quantified as follows. 200 ul of the coated particle solution was pipetted out into a centrifugal vial whose mass was pre-measured. Coated magnetic nanoparticles were captured to the side of the vial wall, and the supernatant was removed. The captured particles were washed with water. At the end, the particles absorbed to the side wall were left to dry in the open vial under a fume hood. The mass of the vial with the dry coated particles were measured. The dry coated particle mass was calculated by subtraction of the mass of the vial from the mass of the vial with the dry coated particles inside. To measure the mass of the particles before coating, uncoated particles corresponding to the same amount of the magnetic material as in the coated nanoparticles, assuming an 80% coating processing yield, was captured to the side of the vial, and dried. The dry mass of the particles before coating was measured by subtraction of the mass of the vial from the mass of the vial with the dry uncoated particles inside. The mass of the coating was equal to the mass of the dry coated particles minus the dry mass of particles before coating.

TABLE 1

| Average Core mass (n = 3) | 0.67 mg |
|---|---|
| Average Coating mass (n = 3) | 0.06 mg |

The total volume of the coating was calculated using the number of large particles in the above mass multiplied by the volume of the coating of each individual large nanoparticles. The particles were suspended in an aqueous solution, and the volume of the coating of each large particle was calculated as $4/3 \times \pi (R_{with\ coating}^3 - R_{core}^3)$, in which the $R_{with\ coating}$ of an individual large nanoparticle was measured using dynamic light with coating scattering (DLS) technique, and the $R_{core}$ of the large core particle was directly imaged core and measured using TEM (see FIG. 5).

TABLE 2

| Average size of large core nanoparticles under TEM | 210 nm |
|---|---|
| Average size of coated large nanoparticles under DLS | 217-357 nm |
| Average coating volume of an coated large nanoparticle | $4/3 \times \pi (110^3 - 105^3)$ nm$^3$ |

The number of large particles in the mass was calculated by dividing the total number of small nanoparticles by the number of small nanoparticles in each large nanoparticle. The total number of small nanoparticles was estimated by dividing the mass of total magnetic material by the mass of an individual small nanoparticle (i.e. calculated using the size and density of the small nanoparticle). The number of small nanoparticles in each individual large particle was counted from the TEM micrograph. Hence, the total volume of the coating can be calculated as the volume of coating of a large nanoparticle multiplied by the total number of the large nanoparticles.

TABLE 3

| Core mass | 0.67 mg |
|---|---|
| Density of core | 5.2 kg/m$^3$ |
| Small nanoparticle size | 16 nm |
| Small nanoparticle Volume | $2.1 \times 10^{-24}$ m$^3$ |
| Mass of each small narnoparticle | $1.1 \times 10^{-17}$ mg |
| Number of small particles in the core | $6.1 \times 10^{16}$ |
| Average number of small particle per large particle | 236 |
| Number of large particles in the core | $2.6 \times 10^{14}$ |
| Total volume of the coating | $4/3 \times \pi (110^3 - 105^3)$ nm$^3 \times 2.6 \times 10^{14}$ = $0.1875 \times 10^{-6}$ m$^3$. |

The density of the coating was calculated using the mass of the coating divided by the total volume of the coating, i.e., 0.06 mg/0.1875×10$^{-6}$ m$^3$=0.32 mg/cm$^3$.

The density of the low density siliceous structure prepared herein is only 0.32 mg/cm$^3$, which is significantly lower than the density of some reported silica coatings, for example, those reported in Vincent et al (Vincent, A. et al, J. Phys. Chem. C 2007, 111, 8291-8298), that have a density of 1-2 g/cc and are 10$^4$ denser than the siliceous structure provided herein.

Characterization of Porosity Using BET Method:

Large magnetic nanoparticles after coating were captured to the side of the vial and dried. 2 samples of 65 mg (sample 1) and 45 mg (sample 2) dry mass were prepared for the BET measurement.

Surface pore sizes were measured using BET method for the dry mass of the coated nanoparticles. The results are shown in the below Tables.

TABLE 4

Characterization for Sample 1

| | |
|---|---|
| Surface Area | 14.166 m²/g |
| Total pore volume for pores smaller than 677.5 Å (Radius) at $P/P_0 = 0.98562$ | $7.562 \times 10^{-2}$ cc/g |

TABLE 5

Characterization for Sample 2

| | |
|---|---|
| Surface Area | 6.380 m²/g |
| Total pore volume for pores smaller than 683.3 Å (Radius) at $P/P_0 = 0.98575$ | $7.099 \times 10^{-2}$ cc/g |

The surface area and the pore volume of the porous nanostructure were measured with dry mass of the porous nanostructure. If measured with a porous nanostructure sample suspended in an aqueous solution, the pore volume and the surface area are expected to be much higher than the measurements with the dry mass, as the density of the coating has been shown to be at least $10^4$ lower than those reported in the art.

The measured density based on the dry power samples does not reflect the real density of the 3-D structure because of the ultralow density of the 3-D structure, the framework easily collapses during the drying process, hence providing much smaller numbers in the porosity measurement than when the 3-D structure is fully extended, for example, like when the porous nanostructure is fully extended in a buffer solution.

Example 4

Delivery of Porous Nanostructures to HeLa Cells

Figure 6:
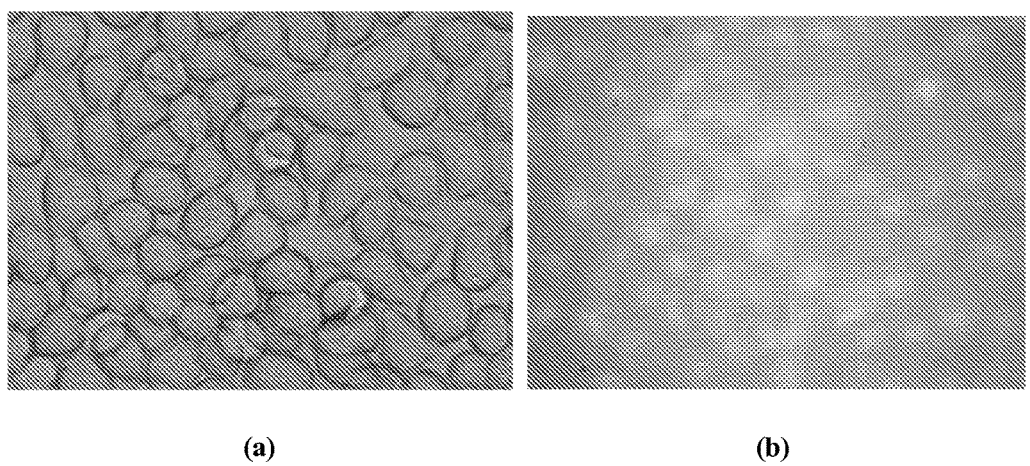
FIG. 6. Alexa 488 Fluorophore labelled DNAs are delivered inside Hela cells using nanoparticles.

The magnetic porous nanostructures as prepared in Example 3 were mixed with alexa-fluorophore 488-DNA using non-covalent approach. After 2 hours incubation, the nanostructures with DNA incorporated were magnetically purified and re-dispersed inside cell culture media. The purified Nanostructure-DNA was then added into the culture medium of HeLa cell culture. After overnight culture of cells, the cell medium (supernatant) was removed, the cells were then washed with PBS. Afterwards, PBS was added into the cell culture well, and images were taken using a fluorescent microscope (FIGS. 6(a) and (b)).

Figure 7:
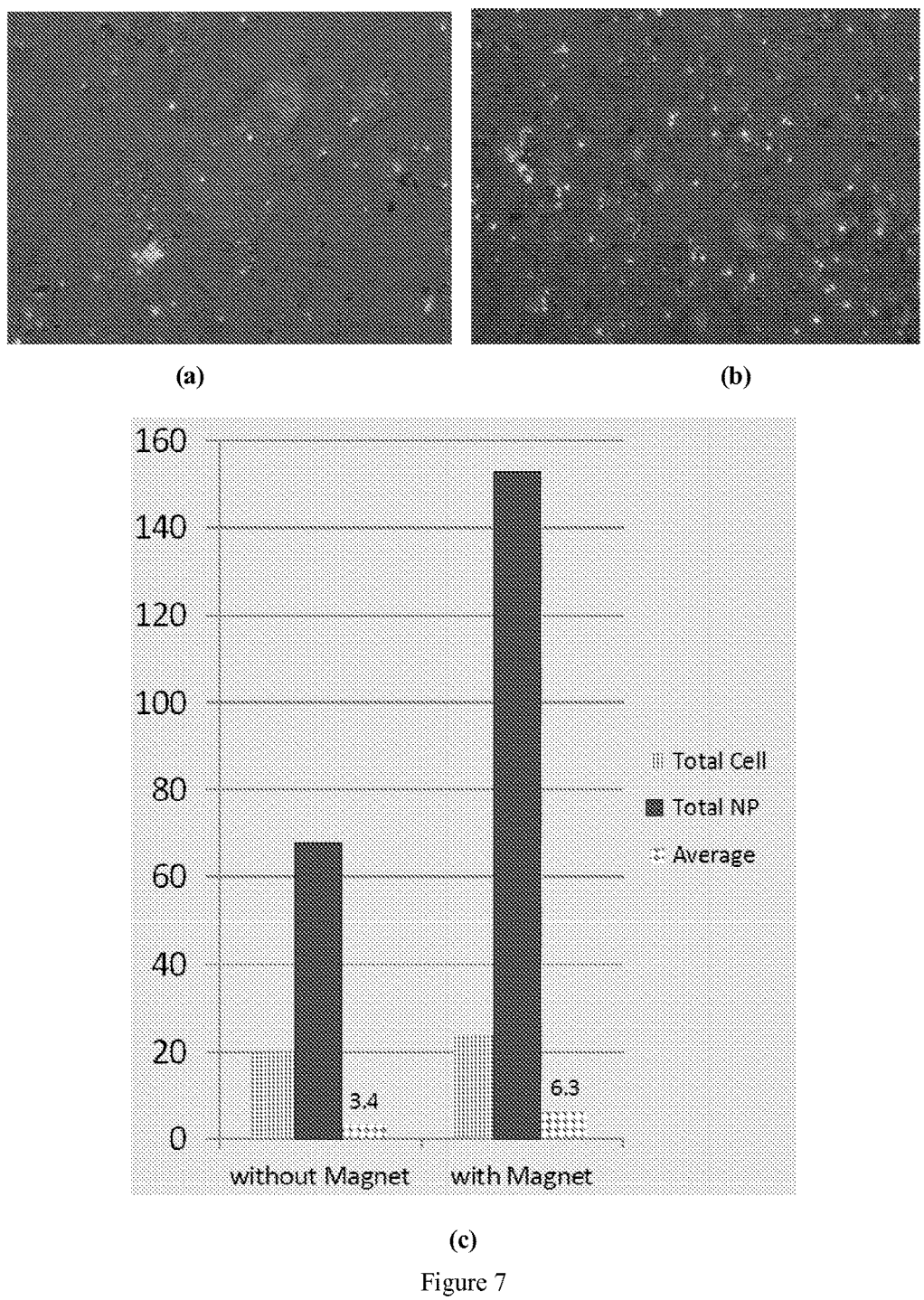
FIG. 7. Additional magnetic force increases the quantity of nanoparticles delivered inside Hela cells. Magnetic nanostructures incorporated with DNA and fluorescent material were incubated with HeLa cells with or without placement of a magnet.

Next, the DNA delivery in the presence and in the absence of magnetic filed was compared. The Nanostructure-DNA was prepared and purified as described above. Two HeLa cell cultures were prepared, and an equal quantity of the Nanostructure-DNA was mixed with the cell culture medium of each of the HeLa cell cultures. One HeLa cell culture was put inside incubator without magnet. Another HeLa cell culture was put inside incubator while a permanent magnet was placed underneath the cell culture well for 4 hours, then removed, and the cell culture plate was left inside the incubator. On the second day, the cell culture medium supernatants for both samples were removed, cells were washed. Then PBS was added into both cell culture wells, and cells were imaged and counted. FIG. 7(a) shows the image of the sample incubated in the absence of a magnet, and FIG. 7(b) shows the image of the sample incubated in the presence of a magnet. As shown in FIGS. 7(a) and 7(b), the fluorescence signal is much stronger in the sample incubated with a magnet than without a magnet. A representative field for each sample was selected under the microscope, and the total number of cells in the field was counted, the total number of nanostructures inside the cells was counted, and the average number of nanostructures per cell was calculated. The results were summarized in FIG. 7(c), which indicates that magnet placement greatly increased the delivery of the magnetic nanostructures inside the cells.

Example 5

In Vivo Delivery of Porous Nanostructures to a Tumor in a Mouse Model

Porous nanostructures are prepared according the methods described in Example 1. Both mercapto and amino groups are incorporated onto the nanostructure surface. A NHS(N-hydroxysulfosuccinimide) modified fluorophore Cy5.5 is conjugated to the amino groups on the surface of the nanostructure. A small cyclo[Arg-Gly-Asp-D-Tyr-Lys] (RGD) peptide is conjugated to the mercapto groups on the surface of the nanostructure, though a SMCC linker (sulfosuccinimidyl 4-[N-maleimidomethyl]cyclohexane-1-carboxylate). The RGD peptide specifically targets a tumor angiogenesis marker $\alpha_v\beta_3$, and causes apoptosis of tumor vessels and promotes tumor regression. The resulting nanostructure is further characterized with TEM, and the density is characterized according to methods described in Example 3.

A SCID mice is implanted with a dorsal skinfold chamber on its back (see, for example, Lehr, H. A., et al, Am J. Pathol. 1993 October; 143(4): 1055-1062), and EGFP transfected human tumor cells are inoculated directly on top of the skinfold. After 10 days growth, the porous magnetic nanostructure loaded with RGD peptide is intravenously injected in the mouse tail vein, and the mouse is examined under an intravital microscope. Images are obtained to show the Cy5.5 fluorescence of the nanostructure, and the EGFP fluorescence of the transfected tumor, where the fluorescence of nanostructure outlines the vessel structures in the tumor. A magnetic bar (NdFeBN52) is placed beneath the dorsal skinfold chamber to apply the magnetic force. A Ni micromesh is placed on top of the chamber to strengthen the magnetic field on the top. Images are taken, which show the Cy5.5 fluorescence for the nanostructure is concentrated below the Ni micromesh, where magnetic field is strong.

Tumor regression is measured for 15 days, with magnetic targeting in the treatment group, and without magnetic targeting in the control group. Images are taken for the tumor area each day, and the tumor regression rate is calculated based on the intensity of the EGFP fluorescence representing the tumor cells. Results show the tumor regression is significantly higher in the presence of magnetic targeting than in the absence.

The invention claimed is:

1. A composition comprising a payload-carrying nanostructure and a biological sample, wherein the payload-carrying nanostructure comprises at least one core nanoparticle coated with a low density porous 3-D structure having a density of <1.0 g/cc determined from dry mass of the 3-D structure divided by the total volume of such 3-D structure in an aqueous solution, wherein the low density porous 3-D structure is made of organosilanes.

2. A method of delivering at least one agent unto or into or onto or cross a biological sample comprising a step of contacting a biological sample with a payload-carrying nanostructure, wherein the payload-carrying nanostructure comprises at least one core nanoparticle or coated with a low density porous 3-D structure having a density of <1.0 g/cc determined from dry mass of the 3-D structure divided by the total volume of such 3-D structure in an aqueous solution, wherein the low density porous 3-D structure is made of organosilanes.

3. The method of claim 2, wherein the nanostructure has magnetic property so as to enhance the delivery using magnetic interaction.

4. The method of claim 2, wherein the payload-carrying nanostructure comprises a first payload.

5. The method of claim 4, wherein the first payload is selected from the group consisting of a targeting moiety, a binding partner, a detectable agent, a biological active agent, a drug, a therapeutic agent, a radiological agent, a chemological agent, a small molecule drug, a biological drug and any combination thereof.

6. The method of claim 4, wherein the payload-carrying nanostructure further comprises a second payload.

7. The method of claim 6, wherein the first payload and the second payload are randomly or orientedly distributed in the nanostructure.

8. The method of claims 4, wherein the first payload is selected from the group consisting of a targeting moiety and a binding partner.

9. The method of claim 6, wherein the second payload is selected from the group consisting of a detectable agent, a biological active agent, a drug, a therapeutic agent, a radiological agent, a chemological agent, a small molecule drug, a biological drug and any combination thereof.

10. The method of claim 2, wherein the surface of the nanostructure is modulated with molecular entities that facilitate the delivery function, wherein as the entities improve specific targeting functions, reduce non-specific association, or adjust the density of payloads on surface.

11. The method of claim 2, wherein the thickness of the nanostructure is tailored from 1 nm to 1000 nm to optimize its delivery function.

12. The method of claim 2, wherein the charge of the nanostructure is tuned to optimize its delivery function.

13. The method of claim 2, wherein the nanostructure is biocompatible and can be formed by a biocompatible component material.

14. The method of claim 2, wherein the nanostructure is biodegradable.

15. The method of claim 2, wherein the payload is released into the biological sample via electrostatic principals, biological or enzymatic interactions, or through photo, pH, thermal, or electronic sensitive bonds.

16. A method of delivering at least one agent into a target site in a subject, comprising administering a payload-carrying nanostructure into a subject, and attracting the payload-carrying nanostructure to the target site in the presence of an applied magnetic field, wherein the payload-carrying nanostructure comprises at least one core nanoparticle coated with a low density porous 3-D structure having a density of <1.0 g/cc determined from dry mass of the 3-D structure divided by the total volume of such 3-D structure in an aqueous solution, wherein the low density porous 3-D structure is made of organosilanes.

17. The composition of claim 1, wherein the payload-carrying nanostructure has a payload.

18. The composition of claim 17 wherein the payload-carrying nanostructure has been delivered into or onto the biological sample.

19. The composition of claim 18 wherein the payload is selected from the group consisting of a targeting moiety, a binding partner, a detectable agent, a biological active agent, a drag, a therapeutic agent, a radiological agent, a chemological agent, a small molecule drag, a biological drag and any combination thereof.

20. The composition of claim 19 wherein the biological sample is a cell, a tissue, organ, or an animal.

* * * * *